United States Patent [19]
Kleid et al.

[11] Patent Number: 4,659,669

[45] Date of Patent: Apr. 21, 1987

[54] MICROBIAL EXPRESSION OF HUMAN INFLUENZA HEMAGGLUTININ PROTEINS

[75] Inventors: Dennis G. Kleid, San Mateo; Debi P. Nayak, Los Angeles; Alan R. Davis, Culver City, all of Calif.

[73] Assignees: Regents of the Univ. of California, Berkeley; Genentech, Inc., S. San Francisco, both of Calif.

[21] Appl. No.: 239,301

[22] Filed: Mar. 2, 1981

[51] Int. Cl.[4] .................. C12N 15/00; C12N 1/20; C12N 1/00; C07H 21/04; C12P 21/00; C12P 21/02; C12P 19/34

[52] U.S. Cl. ........................ 435/243; 435/68; 435/70; 435/91; 435/172.3; 435/253; 435/317; 536/27; 935/12; 935/29; 935/41; 935/72; 935/73

[58] Field of Search ............ 435/68, 70, 91, 172, 435/253, 317, 235, 172.3, 243; 536/27; 935/12, 29, 41, 73

[56] References Cited

U.S. PATENT DOCUMENTS 4,357,421 11/1982 Emtage et al. ................. 435/68

OTHER PUBLICATIONS

Jou et al: Cell 19, 683 (1980).
Gething et al: Nature 287, 301 (1980).
Both et al: Nucl. Acids Res. 8, 2561 (1980).
Brownlee: in *Expression of Eukaryotic Viral and Cellular Genes*, Pettersson et al. (ed.), Academic Press, 1981, pp. 129–140.
Sleigh et al: Nucl. Acids Res. 7, 879 (1979).
Sleigh et al: in *Structure and Variation in Influenza Virus*, Laver et al (ed.), Elsevier/North Holland, New York, 1980, pp. 69–78.
Tacon et al: Molec. Gen. Genet. 177, 427 (1981).
Chang, et al., Nature 275, 617–24 (1978).
Goeddel, et al., Nucleic Acids Res. 8, 4057–74 (1980).
*Structure and Variation in Influenza Virus*, Laver, G. and Air, G., eds., Elsevier North Holland, Inc., New York, N.Y., 1980, 295–307.
The Cloning and Expression in Escherichia coli of an *Influenza Haemagglutinin Gene*, Laver, G. and Air, G., eds., Elsevier North Holland, Inc., New York, N.Y. 1980, pp. 157–168.
*Comparison of the Haemagglutinin Genes of Human H2 and H3 and an Avian Havl Influenza A Subtype*, Laver, G. and Air, G., eds., Elsevier North Holland, Inc., New York, N.Y., 1980, pp. 385–390.
Hiti, et al., Virology 111, 113–124 (1981).
Davis, et al., Gene 10, 205 (1980).
Klenow, et al., Proc. Nat. Acad. Sci. USA, 65, 168 (1970).
Seeburg, et al., Nature 270, 486 (1977).
Maxam, et al., Proc. Nat. Acad. Sci. USA, 74, 560 (1977).
Goeddel, Nature 281, 544 (1979).
Itakura, et al., Science 198, 1056–63 (1977).
Clarke, et al., Methods in Enzymology 68, 436 (1979).
Miozzari, et al., Bacteriology 133, 1457 (1978).
Goeddel, et al., Nature 287, 411 (1980).
Wetzel, et al., Biochemistry 19, 6096 (1980).
Jackson, et al., Virology 93, 458 (1979).
Shine, et al., Nature 285, 456 (1980).
Birnboim, et al., Nucleic Acids Res. 7, 1513 (1979).
Mozes, et al., Proc. Nat. Acad. Sci. USA 77, 4933 (1980).
Crea, et al., Proc. Nat. Acad. Sci. USA 75, 5765 (1978).
Markwell, et al., Biochemistry 17, 4807 (1978).
Lamb, et al., Virology 91, 60 (1978).
Emtage, et al., Nature 283, 171 (1980).
Backman, et al., Proc. Nat. Acad. Sci. USA 73, 4174 (1976).
Clewell, et al., J. Bacteriology, 110, 667 (1972).

*Primary Examiner*—Martinell, James
*Attorney, Agent, or Firm*—Flehr, Hohbach, Test, Albritton & Herbert

[57] ABSTRACT

Disclosed herein are methods and means for microbially expressing human influenza hemagglutinin proteins, useful in the preparation of vaccines, by recombination of DNA gene sequences coding for hemagglutinin protein with microbially operable promoter-operator DNA and transformation of microbial host therewith.

10 Claims, 16 Drawing Figures

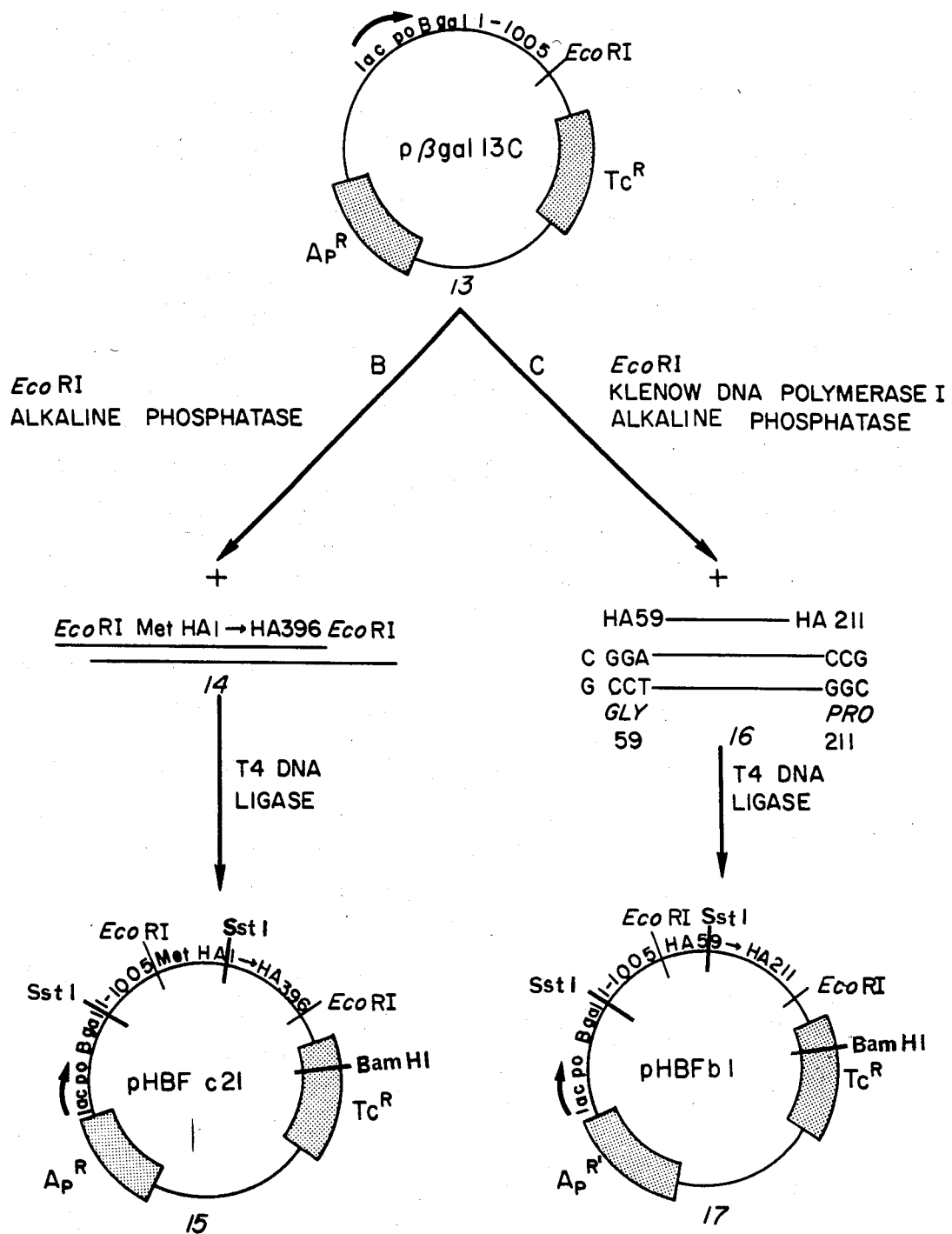
FIG. 3b,c.

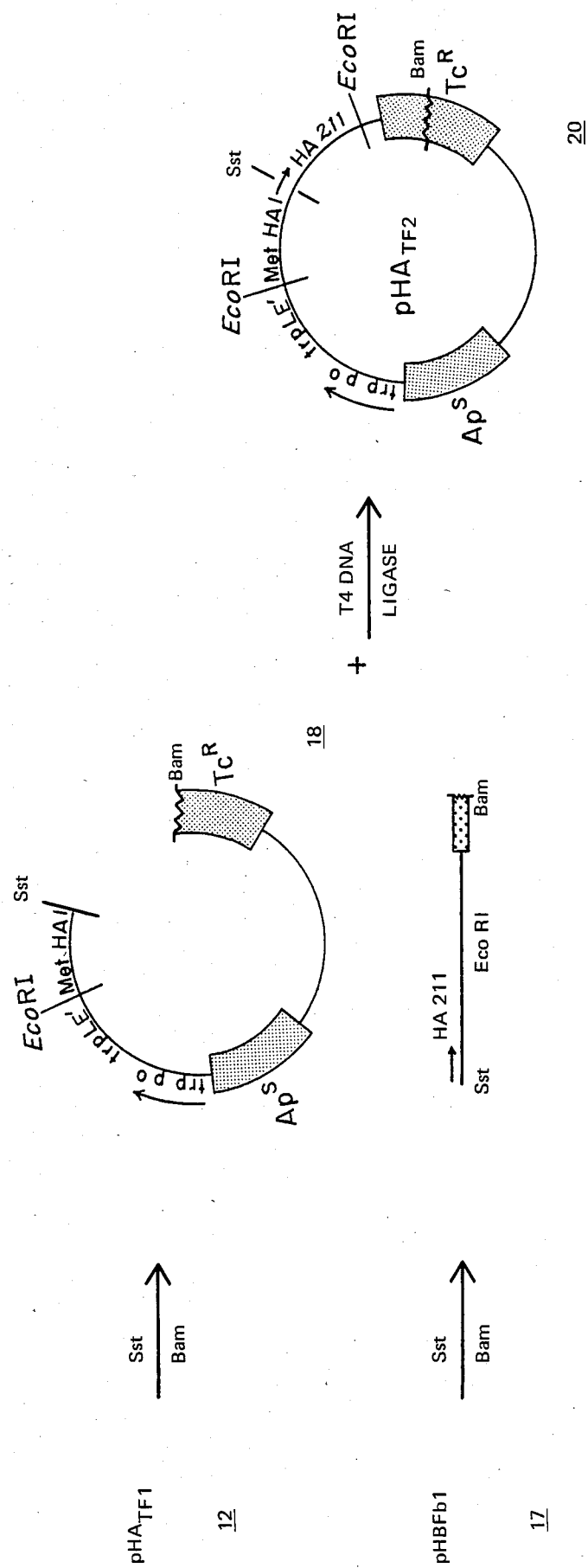

MICROBIAL EXPRESSION OF HUMAN INFLUENZA HEMAGGLUTININ PROTEINS

FIELD OF THE INVENTION

This invention relates to the use of recombinant DNA technology for the microbial production of human influenza hemagglutinin proteins for use in the preparation of vaccines for treating human influenza. In one aspect, the present invention relates to the construction of microbial expression vehicles containing DNA coding for the antigenic determinants of the hemagglutinin gene of human influenza and to the expression vehicles so constructed. In another aspect, the present invention relates to the means and methods for microbially expressing the antigenic determinant(s) of the hemagglutinin gene of human influenza. In yet another aspect, this invention relates to the novel end products of the microbial expression referred to above and to the means and methods of converting such products to entities useful against human influenza.

BACKGROUND OF THE INVENTION

A. Human Influenza Hemagglutinin Proteins

Influenza is a major, acute respiratory disease of human beings. It occurs in recurrent endemic and pandemic infections which start abruptly, spread rapidly and distribute frequently worldwide. Although the disease is usually relatively mild in healthy individuals, its results cause major financial losses from lost time at work and unaccountable impact in terms of pain and suffering. Thus, the prevention of outbreaks of influenza would be of great economic and social value.

The disease is caused by a virus vector which invades and infects host organism cells, disrupting their useful functions. Vaccines for use against influenza, prepared from killed virus, have been in use since the early 1940s. However, the usefulness of these vaccine products has been hampered by several problems such as:

(a) recipients of vaccine innoculations have not always reacted with protective effect, (b) the potency of such vaccines has been variable from batch to batch and virus type to type, (c) the administration of (frequently required) large amounts of vaccine produces adverse reactions often exceeding the tolerable limits of the human organism, (d) their method of production from chick embryos (eggs) can cause incidental toxic effects because of unremovable egg impurities, and (e) search for a suitable live attenuated influenza virus vaccine has not yet been successful because of possible reversion of such virus to wild type during administration into the human population.

These and other factors influence their widespread use and influenza remains as a dreadful disease and those individuals in the elderly age group and/or those who have chronic physical ailments are often susceptible to a greater degree. Thus, it would be very desirable to have a vaccine product for human influenza which, because of the method by which it is prepared, and its constituency, would overcome these problems.

The hemagglutinin (HA) protein is the most important protein involved in immunity against influenza virus. The hemagglutinin protein occurs as glycoprotein spikes on the virus surface. It has been shown to be structurally triangular and rod-shaped and is comprised of several subunits which contain the major antigenic and immunogenic determinants. The antigenic determinants are the antigenic binding sites for specific antibodies. The stimulated production of specific antibodies produces a state within the host organism of immunity to viruses containing the same antigenic determinants. Once induced, these antibodies can remain in the host organism for a significant period of time and later their production can be readily stimulated by reimmunization.

The various subunits of the hemaggluttinin protein are synthesized as part of a single polypeptide chain containing an amino acid precursor peptide attached at the N-terminus of the overall HA protein. Studies have shown that one of these units, referred to as HA1, which is located at the N-terminus of the uncleaved HA is the primary area of the HA molecule which contains the major antigenic determinants. There are a large number of strains and types of influenza viruses. They are distinct from one another by virtue of possessing variations in the antigenic determinants. These variations are referred to as "shifts" and "drifts" depending upon the extent of genetic variation. Thus, antibodies induced from one strain or type do not necessarily protect the host from a different strain. The variations in the antigenic determinants, referred to above, are due to mutations as well as reassortment in the viral genome that in turn lead to amino acid substitutions within the antigenic sites of the HA protein.

Reference is made to *Structure and Variation in Influenza Virus*, Proceedings of the International Workshop on Structure and Variation in Influenza Virus, Thredbo, Australia, Dec. 10-12, 1979, published by Elsevier North Holland, Inc., New York, N.Y., 1980, Editors: Graeme Laver and Gillian Air, in order to further illuminate the background of the present invention and to provide additional detail respecting its practice. By this reference, this citation is hereby incorporated herein.

Thus, it would be desirable to produce vaccines which can be readily modified to account for naturally occurring changes in the various viral strains, by focusing on the hemagglutinin protein itself, determining its, or at least its antigenic determinants', sequence(s) and preparing a vaccine containing the new or changed protein. The present mention provides the methods and means therefor.

B. Recombinant DNA Technology

With the advent of recombinant DNA technology, the controlled bacterial production of useful polypeptides has become possible. The workhorse of recombinant DNA technology is the plasmid, an extrachromosomal loop of double-stranded DNA found in bacteria, oftentimes in multiple copies per bacterial cell. Included in the information encoded in the plasmid DNA is that required to reproduce the plasmid in daughter cells (i.e., a "replicon") and ordinarily, one or more selection characteristics, such as resistance to antibiotics, which permit clones of the host cell containing the plasmid of interest to be recognized and preferentially grown in selective media. The utility of plasmids, which can be recovered and isolated from the host microorganism, lies in the fact that they can be specifically cleaved by one or another restriction endonuclease or "restriction enzyme," each of which recognizes a different site on the plasmidic DNA. Thereafter heterologous genes or gene fragments may be inserted into the plasmid by endwise joining at the cleavage site or at reconstructed ends adjacent to the cleavage site.

As used herein, the term "heterologous" refers to a gene not ordinarily found in, or a polypeptide sequence ordinarily not produced by, the host microorganism whereas the term "homologous" refers to a gene or polypeptide which is produced in the host microorganism, such as E. coli. DNA recombination is performed outside the microorganisms but the resulting "recombinant" plasmid can be introduced into microorganisms by a process known as transformation and large quantities of the heterologous gene-containing recombinant plasmid obtained by growing the transformant. Moreover, where the gene is properly inserted with reference to portions of the plasmid which govern the transcription and translation of the encoded DNA message, the resulting plasmid or "expression vehicle," when incorporated into the host microorganism, directs the production of the polypeptide sequence for which the inserted gene codes, a process referred to as expression.

Expression is initiated in a region known as the promoter which is recognized by and bound by RNA polymerase. In some cases, as in the trp operon discussed infra, promoter regions are overlapped by "operator" regions to form a combined promoter-operator. Operators are DNA sequences which are recognized by so-called repressor proteins which serve to regulate the frequency of transcription initiation at a particular promoter. The polymerase travels along the DNA, transcribing the information contained in the coding strand from its 5' to 3' end into messenger RNA which is in turn translated into a polypeptide having the amino acid sequence for which the DNA codes. Each amino acid is encoded by a unique nucleotide triplet or "codon" within what may for present purposes be referred to as the "structural gene," i.e. that part which encodes the amino acid sequence of the expressed product. After binding to the promoter, the RNA polymerase first transcribes nucleotides encoding a ribosome binding site, then a translation initiation or "start" signal (ordinarily ATG, which in the resulting messenger RNA becomes AUG), then the nucleotide codons within the structural gene itself. So-called stop codons, if present, are transcribed at the end of the structural gene whereafter the polymerase may form an additional sequence of messenger RNA which, because of the presence of the stop signal, will remain untranslated by the ribosomes. Ribosomes bind to the binding site provided on the messenger RNA, in bacteria ordinarily as the mRNA is being formed, and themselves produce the encoded polypeptide, beginning at the translation start signal and ending at the previously mentioned stop signal. The desired product is produced if the sequences encoding the ribosome binding site are positioned properly with respect to the AUG initiator codon and if all remaining codons follow the initiator codon in phase. The resulting product may be obtained by lysing the host cell and recovering the product by appropriate purification from other microorganism protein(s).

C. Promoter-Operator Systems

As examples, the beta lactamase and lactose promoter-operator systems have been commonly used to initiate and sustain the microbial production of heterologous polypeptides. Details relating to the make-up and construction of these promoter-operator systems have been published by Chang et al., Nature 275, 617–24 (1978) and Itakura et al., Science 198, 1056–63 (1977), which are hereby incorporated by reference. More recently, a system based upon tryptophan, the so-called trp promoter-operator system, has been developed. Details relating to the makeup and construction of this system have been published by Goeddel et al. Nucleic Acids Res. 8: 4057-74 (1980), which is hereby incorporated by reference.

The particular trp promoter-operator system has been constructed having a sequence of double-stranded DNA comprising a trp promoter-operator, nucleotides coding for the trp leader ribosome binding site, and in phase from a first 5' to a second 3' end of the coding strand, nucleotides encoding translation initiation for expression of a structural gene that encodes the amino acid sequence of the heterologous polypeptide. The DNA sequence referred to contains neither a trp attenuator region nor nucleotides coding for the trp E ribosome binding site. Instead, the trp leader ribosome binding site is efficiently used to effect expression of the information encoded by an inserted gene. Cells are transformed by addition of the trp promoter-operator-containing and attenuator-lacking plasmids and grown up in the presence of additive tryptophan. The use of tryptophan-rich media provides sufficient tryptophan to essentially completely repress the trp promoter-operator through trp/repressor interactions, so that cell growth can proceed uninhibited by premature expression of large quantities of heterologous polypeptide encoded by an insert otherwise under the control of the trp promoter-operator system. When the recombinant culture has been grown to the levels appropriate for industrial production of the polypeptide, on the other hand, the external source of tryptophan is removed, leaving the cell to rely only on the tryptophan that it can itself produce. The result is mild tryptophan limitation and, accordingly, the pathway is derepressed and highly efficient expression of the heterologous insert occurs, unhampered by attenuation because the attenuator region has been deleted from the system. In this manner, the cells are never severely deprived of tryptophan and all proteins, whether they contain tryptophan or not, can be produced in substantial yields. This system is described in more detail by Kleid et al., U.S. patent application Ser. No. 133,296, filed Mar. 24, 1980, which is hereby incorporated by reference.

D. Prior Art

Emtage et al., Nature (London) 283, 171 (1980), describe the gene sequence for the fowl plague virus and allude to its expression to produce the corresponding fowl plague hemagglutinin protein in a bacterial plasmid whose transcription is under control of a promoter derived from the tryptophan operon. See also German Offenlegungsschrift 3012303. In *Structure and Variation in Influenza Virus,* Supra., beginning on page 157, the same workers report on "The Cloning and Expression in *E. coli* of an Influenza Hemagglutinin Gene." In these publications, Emtage et al. essentially describe the construction of a plasmid vehicle that is designed for the expression of the hemagglutinin protein of fowl plague virus comprising sequences translated from dA:dT tails and linker, a prepeptide, the amino acid sequence of the entire fowl plague virus hemagglutinin comprised of some 560 amino acids and a tail of polypeptide derived from DNA of the pBR322 plasmid. The data presented suggest that the hemagglutinin molecule plus polypeptide presequence is expressed in some degraded form (or proteolytically cleaved form) by use of the tryptophan promoter-operator having an intact attenuator.

BRIEF SUMMARY OF THE INVENTION

The present invention is based upon the discovery that recombinant DNA technology can be used to successfully and efficiently produce portions of the hemagglutinin protein associated with the antigenic determinants of human influenza. These hemagglutinin peptides are microbially expressable, in accordance with the present invention, as stable fusion products with the specific protein of the promoter-operator system employed. In any case, the expressed hemagglutinin peptides hereof lack the prepeptide associated with the precursor to the mature hemagglutinin protein and, in the preferred embodiments, also lack the HA2 sequence and other associated sequences which are not known to be a part of the antigenic determinants. Thus, the designed expression vehicles of the present invention permit the obtention of stable fused protein products which can be readily cleaved in vitro, for example, using cyanogen bromide, to produce the hemagglutinin peptides free of other heterologous and homologous proteins, and preferably also lacking those portions of the molecule which have not been shown to be (important) antigen determinant sites. The expression products of the present invention are microbially produced, recovered, and purified to levels required for use in vaccines designed for the prevention of human influenza.

Representative hemagglutinin peptide products obtained hereby have been shown to bind directly to antibodies and, by in vitro tests, have been shown to contain at least the major antigen determinants of the mature, natural hemagglutinin protein. These tests are predictive of the ability of the hemagglutinin proteins hereof to raise specific antibodies in vivo.

The present invention comprises the human influenza hemagglutinin proteins so produced and the means of producing them. Specifically, the present invention is directed to polypeptide of human influenza hemagglutinin protein comprising the amino acid sequence of at least one antigenic determinant of mature human influenza hemagglutinin protein, microbially produced and in substantially biologically pure form, optionally containing at the N-terminus, the methionine amino acid and optionally linked thereto a sequence derived from the microbially operable promoter-operator system employed, for example, a sequence of the trp leader polypeptide fused to a portion of trp E polypeptide or a fragment of the β-galactosidase polypeptide. The present invention is further directed to synthetically derived (organic syntheses and/or reverse transcription) gene sequences coding for the polypeptides described above and to replicable microbial expression vehicles containing said gene sequences in expressible form so that said vehicles are capable of expressing the polypeptides described above. Further, the present invention is directed to transformed microorganisms containing the expression vehicles described above. In still further aspects, the present invention is directed to various processes useful in preparing said polypeptides, gene sequences and expression vehicles and to specific embodiments thereof.

The term "human influenza hemagglutinin proteins" embraces all human strains regardless of origin.

BRIEF DESCRIPTION OF THE DRAWINGS

FIGS. 7a,b. A/WSN/33 nucleotide sequence of the "+" strand of gene 4 and amino acid sequences of different subtype hemagglutinins: second line, H0 subtype (A/WSN/33); third line, H2 subtype (A/Japan/305/57); fourth line, H3 subtype (A/Memphis/102/72); fifth line, HAV1 subtype (A/Fowl Plague/Rostock/34). Boxed regions indicate homology between the H0 and H2 subtypes and also complete homology in all strains. The N-terminal amino acids of the $HA_1$ and $HA_2$ chains are capitalized.

DESCRIPTION OF THE PREFERRED EMBODIMENTS

Figure 1:
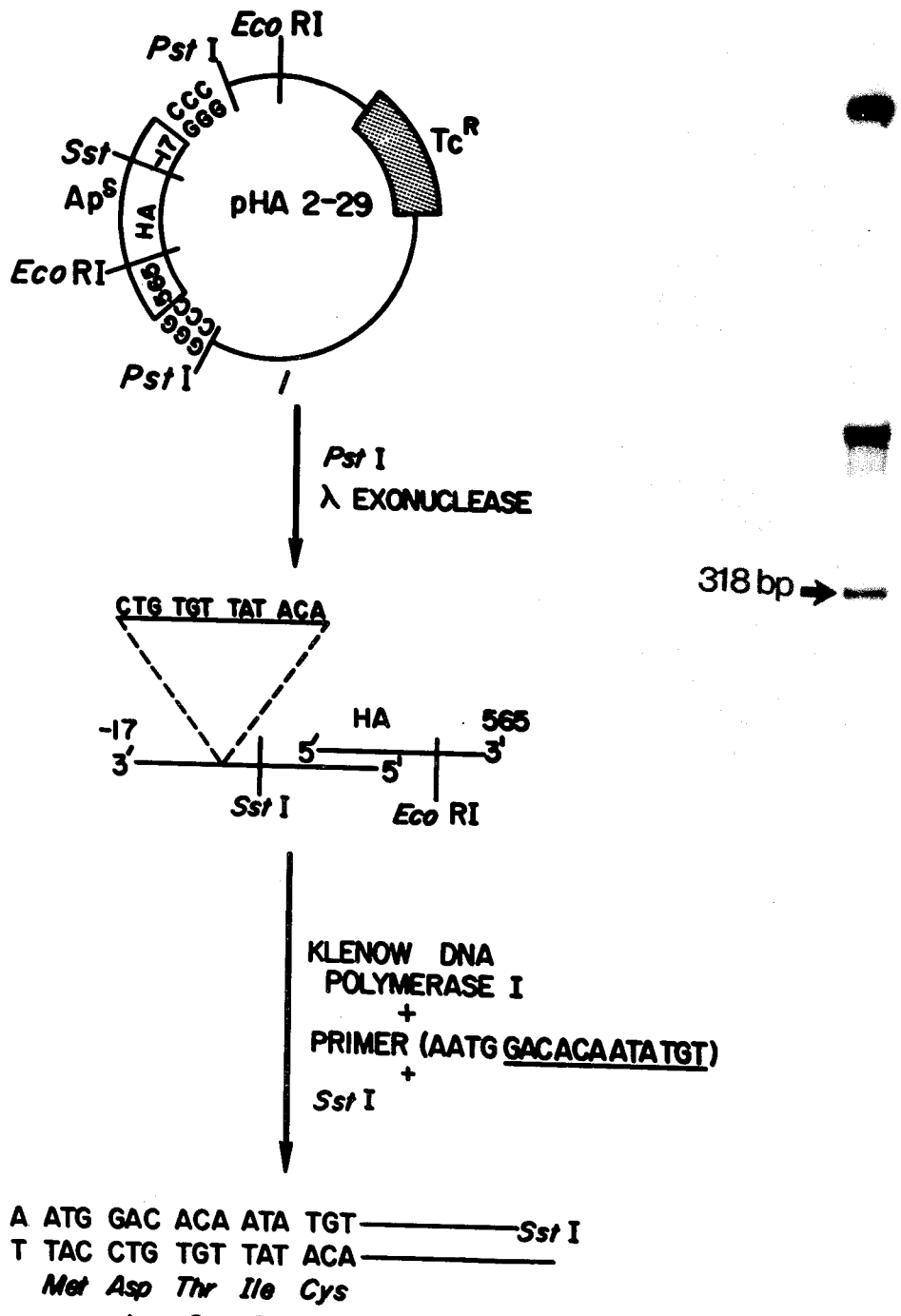
FIG. 1 depicts the construction of a DNA fragment beginning with an ATG initiation codon followed by the coding sequence of the mature influenza hemagglutinin protein. The inset is an autoradiogram of the radioactively labelled gene fragment thus constructed.
Figure 2:
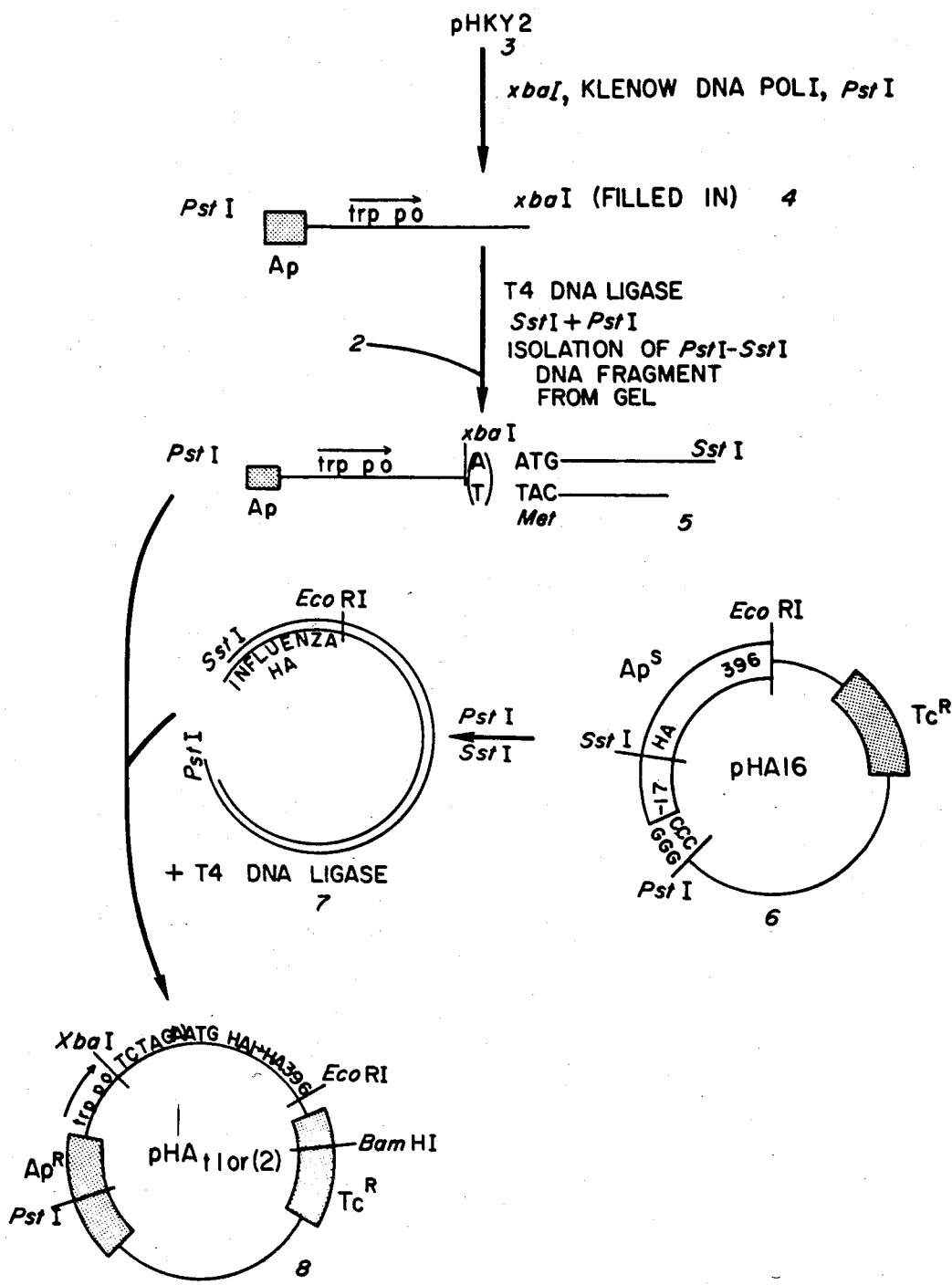
FIG. 2 depicts the construction of plasmid vehicles ($pHA_{t1}$, $pHA_{t2}$) designed to express directly the hemagglutinin protein.

The sequence of the hemagglutinin HA gene A/WSN/33 strain (H0N1) of human influenza virus has been compared with four other HA sequences: the human H2 strain A/Japan/305/5/57, the human H3 strains A/Memphis/102/72 and A/Victoria/3/75 and HAV1 (fowl plague). Details concerning this work are described by Hiti et al., "Complete Sequence Analysis Shows That the Hemagglutinins of the H0 and H2 Subtypes of Human Influenza Virus are Closely Related," *Virology*, 111, 113–124 (1981), which is hereby incorporated by reference. See also the article by Brownlee, "Comparison of the Hemagglutinin Genes of Human H2 and H3 and an Avian HAV1 Influenza A Subtype," *Structure And Variation In Influenza Virus*, published by Elsevier North Holland Inc., New York, 1980, p.385, which is hereby incorporated by reference.

A bacterial plasmid (pHA2-29) was constructed containing the structural gene for the HA of the A/WSN/33 strain (H0N1) of human influenza virus (Davis, et al.) "Construction and Characterization of a Bacterial Clone Containing the Hemagglutinin Gene of the WSN Strain (H0N1) of Influenza Virus," *Gene* 10,205 (1980), which is hereby incorporated by reference. A synthetic dodecadeoxynucleotide primer was used to prepare a double strand DNA form of the hemagglutinin gene of a human influenza virus (A/WSN/33 strain, (H0N1)). This DNA was inserted in the Pst I site of plasmid pBR322 via dG:dC tailing and cloned in bacterial cells. The restriction map of this insert was determined and structurally important areas of the hemagglutinin gene were sequenced. Amino acid sequences of several regions of the hemagglutinin protein were deduced from DNA sequences of the insert and compared to the known amino acid sequences of other HON1 viruses derived by protein sequencing. This work and other details connected with it are described by Davis et al., Supra. The clone contains the entire structural gene and only 13 nucleotides, which are missing at the 3′ end of cRNA, are beyond the poly A addition (or transcription termination) site and therefore are not present in the mRNA. The sequence of the HA insert of this clone has been recently completed (Hiti, et al., Supra). The A/WSN/33 HA gene is 1775 nucleotides in length coding for 565 amino acids. The cRNA contains a 5′ noncoding region of 32 nucleotides, a coding region of 1695 nucleotides and a 3′ non-coding region of 48 nucleotides. The sequence shows a 17 amino acid signal prepeptide at the amino terminus followed by HA1 (325 amino acids), a single arginine connecting residue, and HA2 (222 amino acids) at the carboxy terminus. The sequence contains, at amino acids 153–159, a tryptic peptide shown to be changed in variants of HON1 virus (A/PR8/34) selected with monoclonal antibodies, indicating that this region is an antigenic determinant.

In this invention, gene sequences derived from the H0 hemagglutinin of A/WSN/33 are attached, without the 17 amino acid prepeptide codons, to plasmid expression vehicles. These vehicles are of several types, utilizing two particular, different microbially operable promoter-operator systems. These particular systems employ either the tryptophan operon or the lactose operon. They utilize two methods of expression, either direct expression, beginning with a methionine codon attached to the gene coding for the mature hemagglutinin gene, or the fusion protein method, attaching HA gene sequences in phase with microbially expressed proteins. In particular embodiments described herein, the types of vehicles utilize different parts of the HA coding sequence. One type uses a gene coding for the entire mature protein, that is, codons 1-565, a second type uses codons 1-395, a portion of the coding sequence, a third type uses codons 1-211, and finally a fourth type uses codons 59-211.

The preferred embodiments employ a particular combination of these methods such that the desired protein is expressed efficiently in the microbe and contains at least one and preferably the most important of the several antigenic determinants of the influenza hemagglutinin.

In one embodiment hereof, in order to microbially express human HA antigenic determinants in bacterial cells, the DNA coding for the prepeptide was removed and AUG (codon for methionine, was added before the DNA of the mature HA. This reconstructed DNA was placed behind a bacterial promoter-operator with a bacterial ribosome binding site followed by the codon for methionine. In this way the N-terminal portion of mature HA was fused to bacterial proteins. The antigenicity of a fusion product thus obtained, containing bacterial proteins, was determined and smaller areas of HA1 protein thereof were shown to contain the expected antigen determinants.

DNA coding for antigenic determinants of the hemagglutinin gene of a human influenza was expressed in E. coli. Three types of expression plasmids were constructed. One type directed the expression of amino acids 1 to 396 of the mature hemagglutinin gene joined by a methionine to the first 1,005 amino acids of β-galactosidase. The other was a fusion of the first 1,005 amino acids of β-galactosidase to amino acids 59 to 211 of hemagglutinin, and the third uses the 1005 amino acid β-galactosidase fusion with amino acids 1 to 211 of hemagglutinin. The fusion proteins exhibited binding to antibodies. This binding could be competed by excess hemagglutinin antigen demonstrating the presence of antigenic determinants of hemagglutinin in these fusion proteins. The first expression product competed in degree greater than 90 percent with human influenza virus bound with specific antibodies, indicating the presence in the expression product of the antigenic determinants of mature hemagglutinin.

Two different types of expression plasmids were also constructed. One directed the expression of amino acids 1 to 396 of the mature hemagglutinin gene joined by a methionine to the first 190 amino acids of tryptophan derived operon system. This fusion protein also exhibited binding to antibodies which could be competed by excess hemagglutinin antigen demonstrating the presence of antigenic determinants of hemagglutinin therein. The second directed the expression of amino acids 1 to 211 of the mature hemagglutinin gene joined by a methionine to the first 190 amino acids of the tryptophan operon derived system.

Laver et al., "The Antigenic Sites on Influenza Virus Hemagglutinin. Studies on Their Structure and Variation," *Structure and Variation Influenza Virus*, Supra., p. 295, and Wiley et al., *Nature*, 289, 373 (1981), report on the amino acid sequences of importance with respect to antigen determinants. Specifically, based upon their work, it can be predicted, in general, that amino acids 30 to 275 of the mature hemagglutinin protein contain at least one and probably the most important of the several antigenic determinants. Specifically, they show that amino acids 140 to 146 of A/Memphis/102/72 (H3) represent a site important for an antigenic determinant. This corresponds in structure to amino acids 153 to 159 A/WSN/33 (H0). In accordance with the present invention, it is possible to express each of the human influenza hemagglutinin polypeptides, or portions thereof which contain at least one antigenic determinant site, located as defined above. In the preferred embodiments, these polypeptides are expressible as fusion proteins optionally linked via a methionine amino acid to the first 1,005 amino acids of the β-galactosidase operator or the 190 amino acids of the tryptophan operator-promotor derived system.

DETAILED DESCRIPTION

Construction of a DNA Molecule Coding for Mature HA

The A/WSN HA has a 5′ non-coding region of 32 nucleotides followed by a 17 amino acid signal prepeptide (Davis, et al., Supra; Hiti, et al., Supra.). Since the hydrophobic prepeptide is absent in native HA, the HA antigenic determinants in *E. coli* were expressed without this signal peptide. Therefore, initiation of protein synthesis in *E. coli* must occur at an ATG codon placed before amino acid 1 (Asp) of the mature polypeptide rather than at the ATG codon preceding the prepeptide. To accomplish this pHA2-29 (1, FIG. 1) a plasmid containing the entire HA coding sequence linked to pBR322 by dG;DC tails (Davis, et al., Supra), was digested with PST I and λ exonuclease (FIG. 1). Treatment with this processive 5′-exonuclease removed sequences from the 5'-coding (cDNA) strand. A synthetic deoxynucleotide primer dAATGGACACAATATGT was prepared. This primer contains the coding sequence for methionine followed by that of the first four amino acids of mature HA (Asp-Thr-Ile-Cys). The primer was labelled at its 5'terminus, added to the λ exonuclease treated DNA, heat denatured, and hydridized. The Klenow fragment (Klenow and Henningsen, *Proc. Natl. Acad. Sci. (USA)* 65, 168 (1970) of DNA polymerase 1 was added to catalyze repair of the cDNA strand from the primer, as well as to remove the extending 3'-DNA strand with the associated 3'-5' exonuclease activity of the enzyme, and finally to repair the 5' AATG end of the primer leaving adouble-stranded end

This DNA was cleaved at the Sst I site at 318 bp, fractionated on a polyacrylamide gel, and the desired 318 bp fragment (2, FIG. 1; FIG. 1 inset) was eluted. However, small amounts of other larger and shorter DNA fragments were also observed, possibly due to incomplete removal of 3'-protruding ends and incomplete repair synthesis. The experimental details of the DNA fragment synthesis are given below under examples.

Direct Expression of HA

The following is the description of the construction of plasmid vehicles designed for the direct expression of the mature hemagglutinin, , $pHA_{t1}$, $pHA_{t2}$, pHA26, pH026, and $pHO_{t1}$ (HA vehicles contain codons 1-395 and H0 vehicles contain codons 1-565).

Plasmid pHKY2 (3, FIG. 2), containing the *E. coli* trp promoter-operator (Goeddel, et al., Supra) was cleaved with Xba I and then treated with DNA polymerase I to yield a blunt end. After treatment with Pst I the small fragment containing the trp promoter, operator, and the trp leader ribosome binding site but not its ATG codon, was isolated (4, FIG. 2). This fragment was ligated (Goeddel, et al., Supra.; Kleid, Supra., 1979) through its blunt end to the reconstructed HA DNA (2, FIG. 1) lacking the DNA for the prepeptide. After treatment with Sst I and Pst I to remove dimers formed through ligation of cohesive termini, the correct ligation product (5, FIG. 2) was recovered from a polyacrylamide gel.

To facilitate further construction pHA2-29 (1, FIG. 1) was rearranged by removing the Pst I site after the DNA coding for the C-terminal amino acids of HA2. This was accomplished by isolating two fragments, name a) the 1266 bp Pst I-Eco RI DNA fragment containing DNA coding for amino acids -17 (prepeptide) to 396 (i.e. amino acid 71 of HA2) of pHA2-29 and b) the large 3611 bp Eco RI-Pst I DNA fragment of pBR322. Ligation of these fragments followed by transformation (Seeburg, et al., *Nature* 270, 486 (1977) of *E. coli* K-12 strain 294 (Backman, et al., *Proc. Natl. Acad. Sci.* (*USA*) 73, 4178 1976) and plasmid isolation (Clewell, et al., *J. Bacteriology,* 110, 667 1972) yielded pHA16 (6, FIG. 2). The plasmid pHA16 was then cleaved with Pst I and Sst I and the large Sst I-Pst I fragment (7, FIG. 2) isolated on an agarose gel. Ligation of a DNA fragment containing the junction of bacterial promoter and mature HA DNA (5, FIG. 2) to this Sst I-Pst I adaptor fragment (7, FIG. 2) yielded direct expression plasmids (8, FIG. 2). DNA in the junction region of a number of these plasmids was sequenced by the method of Maxam and Gilbert, *Proc. Natl. Acad. Sci.* (*USA*) 74, 560 (1977). Most of the junctions contained the expected sequence, that is, the trp promoter sequence followed by the filled in Xba I restriction site sequence (TCTAG) followed by the primer sequence. A few, however, were missing one or more nucleotides at the junction site. In particular, $pHA_{t1}$ (8, FIG. 2) was missing one A, having the sequence dTCTAGATG at the junction site. In a similar way plasmid pHA 26 (not shown) was constructed which contained the expected junction of the lac promoter-operator to amino acids 1-396 of mature HA with an intervening ATG initiation codon. This was accomplished by ligating the small DNA fragment from Pst I to Eco RI (filled in) of pGH6 (Goeddel, *Nature* 281, 544 (1979) to DNA fragments 2 (FIG. 1) and 7 (FIG. 2) in the same manner as described above for construction of $pHA_{t1}$. The plasmid pGH6 contains the lac promoter-operator and a ribosome binding site but lacks ATG (Goeddel, et al., Supra (1979).

Cells transformed with trp and lac direct expression plasmids $pHA_{t1}$ or $pHA_{t2}$ (8, FIG. 2) and pHA26 were tested for production of HA antigen in a number of systems. No new proteins were visible in polyacrylamide-SDS gels when compared with cells transformed with pBR322. A small (less than 100 copies/cell) and variable amount of activity was detected in a solid phase radioimmunoassay system (Clarke, et al., *Methods in Enzymology* 68, 436 1979). No specific proteins were immunoprecipitated with anti-WSN IgG in extracts of either $pHA_{t1}$, $pHA_{t2}$, or pHA26. Completion of the HA gene following the trp and lac promoters by insertion of DNA coding for amino acids 396-565 from the Eco R1 to the termination site (pH026 and pHOt1) did not improve expression (Davis and Kleid, unpublished results). If susceptibility to bacterial proteases is the cause of low yields, as suggested previously for direct expression of other proteins in *E. coli* (Itakura, et al., Supra) then fusion to a bacterial protein may stabilize the protein and correct the low yield problem. This approach was also attractive because of a large CNBr peptide (amino acids 1-226 in A/WSN HA) that has been shown to retain immunogenic properties in H3 virus (Jackson et al., *Virology* 89, 199 and 93, 458) and could be isolated from fusion proteins.

Construction of Plasmids that Express HA Fusion Proteins

The following is the description of the construction of plasmid vehicles that express fusion proteins, $pHA_{TF1}$, $pHA_{TF2}$, pHBFb1, pHBFc21 and pHBFd1 ($HA_{TF}$ are trp fusions, HBF are β-galactosidase fusions).

$pHA_{TF1}$

To construct fusion proteins containing amino acids 1-396 of HA, $pHA_{t1}$ (8, FIG. 2) was cleaved with Xbal followed by treatment with S1 nuclease (Davis, et al., Supra) and Bam H1. A DNA fragment containing the sequence of the ATG initiation codon through amino acid 396 of HA and terminating in the Bam HI site of the tetracycline resistance gene of pBR322 was isolated (9, FIG. 3A). A plasmid coding for the gene fusion (12, FIG. 3*a*) was constructed by joining this DNA fragment (9, FIG. 3*a*) to the desired DNA fragment (11, FIG. 3*a*) obtained from pNCV (10, FIG. 3*a*). The pNCV is a plasmid construction containing the trp promoter-operator and the trp L, trp E genes with the deletion trp ΔLE1413 (Miozzari and Yanofsky, *J. Bacteriology* 133, 1457 (1978). Synthetic DNA has been added in this plasmid construction such that the last three amino acid codons and the termination codon (GAG ACT TTC TGA) of the trp E gene have been replaced with the sequence GAATTCTGCAGAATTC (Goeddel, et al., *Nature* 287, 411–416, 1980). This microbially expressed fusion protein derived from the tryptophan operon is referred to herein as the trp LE' gene. The plasmid pNCV (10, FIG. 3a) was cleaved with Pst I and treated with Klenow DNA polymerase I to remove protruding 3'-termini. After treatment with Bam HI the large fragment (11, FIG. 3a) was isolated on a polyacrylamide gel and ligated to DNA fragment 9 (FIG. 3a) to construct the fusion plasmid (12, FIG. 3a). Several plasmids were sequenced in the region of the fusion of the HA to the trp LE' gene. One (pHA$_{TF1}$, 12, FIG. 3a) was found to have the correct sequence with an Eco RI site directly flanking the ATG initiation codon before HA. *E. coli* K-12 strain 294/pHA$_{TF1}$, was grown in rich media then a sample diluted 1 to 20 into media containing very little tryptophan. The microorganism then directed the synthesis of protein from the cellular and plasmid encoded tryptophan promoter-operator systems. The desired fusion protein was detected in polyacrylamide-SDS gels although the amount was low (data not shown).

pHBFc21

Figure 3A:
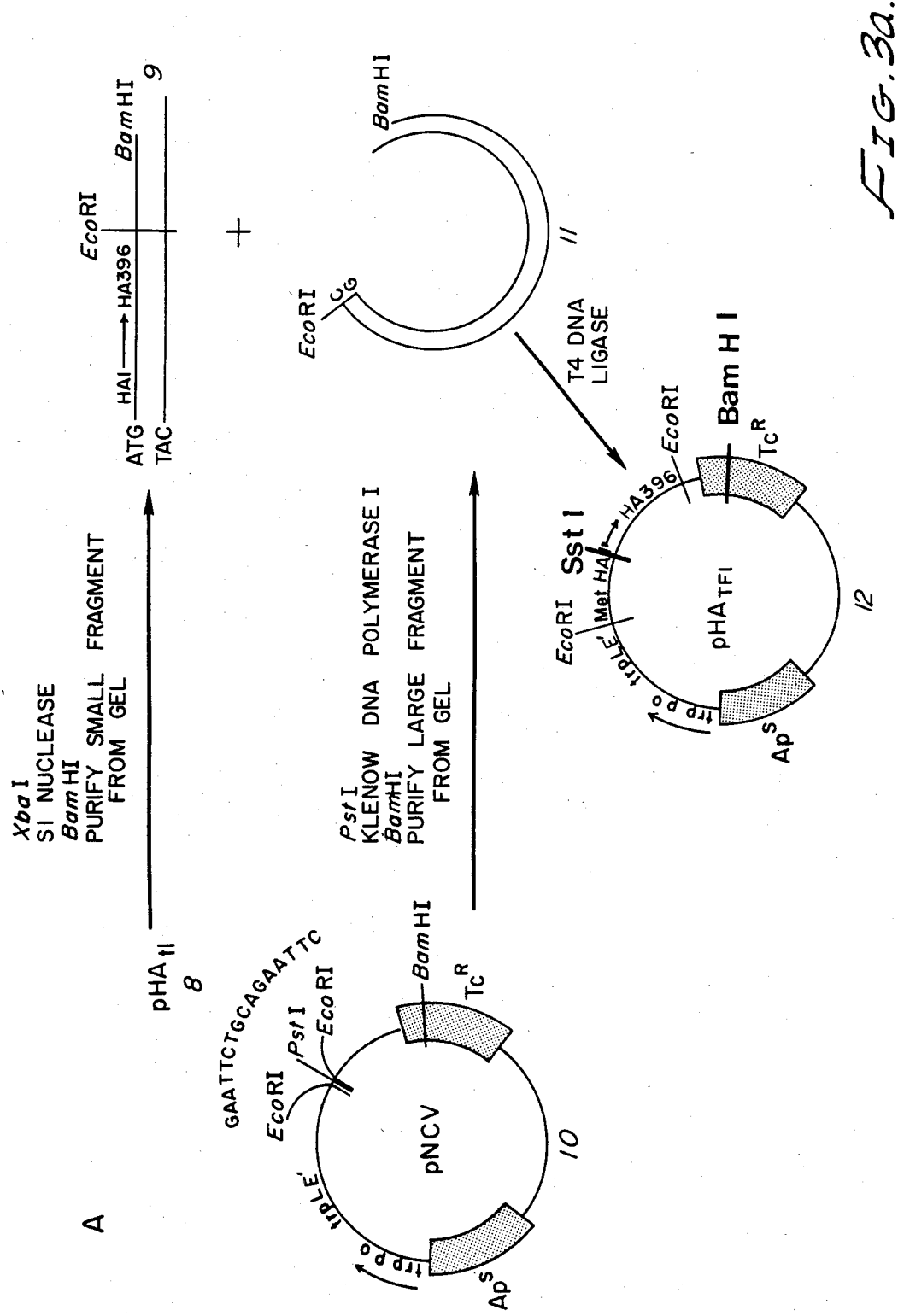
FIGS. 3a, b, c, d and e depict construction of plasmid vehicles ($pHA_{TF1}$, pHBFc21, pHBFb1, $pHA_{TF2}$ and pHBFd1) that express fusion proteins. The proteins thus expressed contain sequences derived from either the E. coli tryptophan operon, or the E. coli β-galactosidase protein, fused to sequences of the antigenic portions of the hemagglutinin protein.

The DNA fragment containing HA was also joined to a larger bacterial protein gene derived from the lac operon. The HA DNA fragment 14 (FIG. 3b) coding for 396 amino acids was joined to a DNA fragment coding for first 1005 amino acids of β-galatosidase. Therefore pHA$_{TF1}$ (12. FIG. 3a) was treated with Eco RI and the small fragment containing the ATG initiation codon through amino acid 396 of HA isolated (14, FIG. 3b). This DNA was ligated to the Eco RI site of pβgal 13C (13, FIG. 3b). The plasmid pβgal 13C is a derivative of pBR322 containing the lac promoter-operator and almost the entire structural gene for β-galactosidase, extending 1005 codons. This plasmid contains a single EcoRI site at the gene sequence coding for amino acid 1005 of the β-galactosidase structural gene. Insertion of the HA DNA fragment preserves the amino acid reading frame of the β-galactosidase structural gene. Small samples of plasmid DNA were screened (Birnborm and Doly, *Nucleic Acids Res* 7, 1513 (1979)) using restriction enzyme analysis for the correct orientation of the EcoRI to EcoRI DNA fragment containing the HA sequence. Of 14 plasmids containing this insert, 5 were found to have the correct orientation. Samples (3 ml) of *E. coli* K-12 strain 294 /pHBFc21 (15, FIG. 3b) with plasmid having the correct orientation and *E. coli* 294/pHBFc20 with plasmid having the incorrect (reverse) orientation were grown and lysates of total cells analyzed on polyacrylamide-SDS gels (FIG. 4d). Only pHBFc21 was found to have new proteins, the largest of which migrated with the β—β" subunits of RNA polymerase (MW 155,000–165,000) as expected for this HA β-galactosidase fusion protein (calc MW=158,600).

pHBFb1

A plasmid was constructed that contained a fusion of the β-galactosidase structural gene in phase with codons 59-211 of HA (FIG. 3c). The plasmid pβgal 13C (13, FIG. 3) was cleaved with EcoRI followed by treatment with Klenow DNA polymerase 1 and then with calf intestine alkaline phosphatase (Davis, et al., Supra) to prevent self-closure. The plasmid pHA2-29 (1, FIG. 1) was cleaved with Hpa II followed by treatment with Klenow DNA polymerase 1 and the HpaII DNA fragment coding for amino acids 59-211 was isolated (16, FIG. 3c). After ligation of the HpaII DNA fragment and transformation, small samples of plasmids were prepared and screened for correct orientation of the HpaII DNA fragment using restriction enzyme analysis. Of 24 plasmids containing this insert, 13 were found to have to correct orientation. Again, small samples of cells with plasmid having the HpaII DNA in the correct orientation (pHBFbl, 17, FIG. 3c) and reverse orientation (pHBFb9) were grown and total proteins analyzed on SDS-polyacrylamide gels (FIG. 4a). Only in the lysate of cells transformed with pHBFb1 was a new protein with the MW of the expected fusion protein (calc. MW 131,639) observed.

pHA$_{TF2}$

A plasmid was constructed that contained a fusion of the trp LE' gene in phase with codons 1-211 of HA (FIG. 3d). The plasmid pHA$_{TF1}$ (12, FIG. 3d) was cleaved with Sst, at a site located within the HA gene sequence and with BAM, at a site located in the Tc$^R$ sequence. The plasmid (18, FIG. 3d) was purified from the small cleavage product by electrophoresis on a polyacrylamide gel. A corresponding Sst to BAM DNA fragment (19, FIG. 3d) was cleaved from pHBFb1 (17) and isolated. This fragment is similar in structure to that removed from pHA$_{TF1}$ except that it does not contain hemagglutinin codons 212-395. The DNA fragments 18 and 19 were joined by T$_4$ Ligase and used to transform *E. coli* K-12 strain 294. Virtually all of the colonies obtained contained the identical plasmid as determined by restriction analysis. This construction is depicted in FIG. 3d as pHA$_{TF2}$. *E. coli* K-12 strain 294/pHA$_{TF2}$ was grown in rich media then a sample diluted 1 to 20 into media containing very little tryptophan. The microorganism expresses the desired fusion protein as determined by polyacrylamide-SDS gels (data not shown).

pHBFd1

Figure 3E:
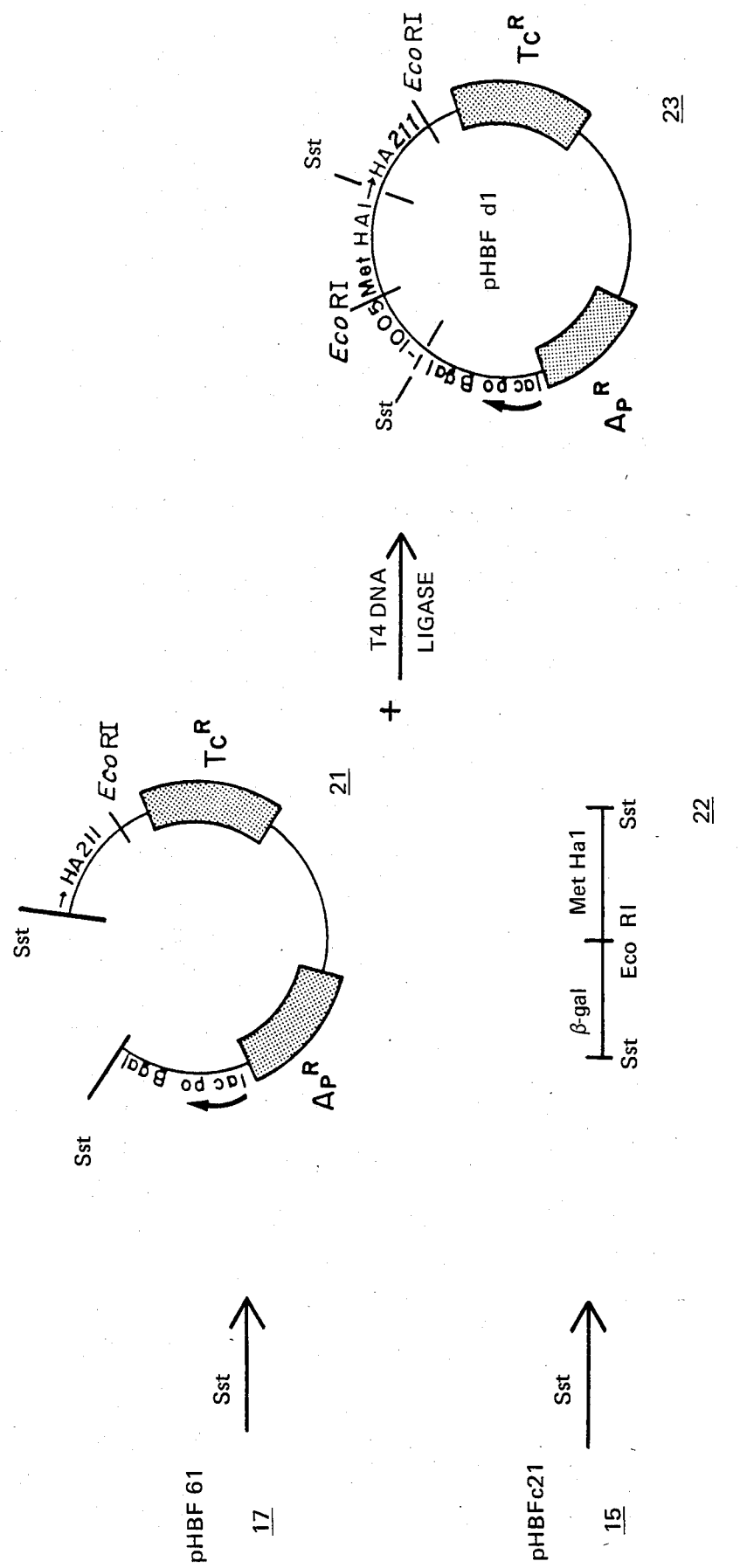

A plasmid was constructed that contained a fusion of the β-galactosidase gene (codons 1-1006) in phase with codons 1- 211 of HA (FIG. 3e). The plasmid pHBFb1 (17) was cleaved with Sst and treated with calf intestine alkaline phosphatase to give the product, 21, shown in FIG. 3e. Similarly pHBFc21 was cleaved with Sst and a DNA fragment 22 isolated. This fragment 22 is similar in structure to that cleaved from 17 except that fragment 22 contains HA codons 1-59 and an initiation codon (ATG), or CNBr cleavable residue (met). The DNA fragments 21 and 22 were joined by T$_4$ ligase and used to transform *E. coli* K-12 strain 294. One plasmid, containing the Sst fragment in the correct orientation (pHBFd1) was used for further study. Lysates of *E. coli* 294/pHBFd1 analysed on polyacrylamide-SDS gels showed a new protein with the expected molecular weight (data not shown).

Characterization of Fusion Protein Expression

In the *E. coli* K-12 strain 294 there is found a number of molecules called the lac repressor. When in sufficient number, the molecules specifically repress synthesis from the lac promoter-operator system. This repression can be inhibited by growth in the presence of IPTG.

The production of both fusion proteins c21 and b1 were tested for response to IPTG. When cells were grown in the presence of 2 mM IPTG the amount of both c21 and b1 fusion proteins increased (FIG. 4b and d). New proteins of lower molecular weight (130-150,000) were also found in total lysates of E. coli 294/pHBFc21.

To determine if the new proteins were present in soluble or in membrane fractions, E. coli 294/pHBFc21 or b1 were grown to late log phase, resuspended in lysis buffer, and sonicated. Lysates were centrifuged 30 min at 27,000×g and proteins in the supernatant and pellet fractions analyzed on SDS-polyacrylamide gels. Results (FIG. 4b) show that as with other β-galactosidase fusion proteins (Goeddel, et al., Supra 1979; Shine, et al., Nature 285, 456 (1980); Wetzel, et al., Biochemistry 19, 6096 (1980)) both proteins c21 and b1 are insoluble and are found in the pellet fraction.

To further characterize these fusion proteins, they were partially purified. Thirty grams (wet weight) of E. coli 294/pHBFb1 and E. coli 294/pHBFc21 were lysed and the chimeric proteins partially purified as described below. Due to their large size, enrichment was obtained on a column of Sephacryl-S200. The column was monitored by eletrophoresis in polyacrylamide-SDS gels and fractions enriched in fusion proteins pooled (data not shown). These enriched fractions were iodinated and used in radioimmune assay.

Immunological Characterization of Fusion Proteins

Figure 5A:
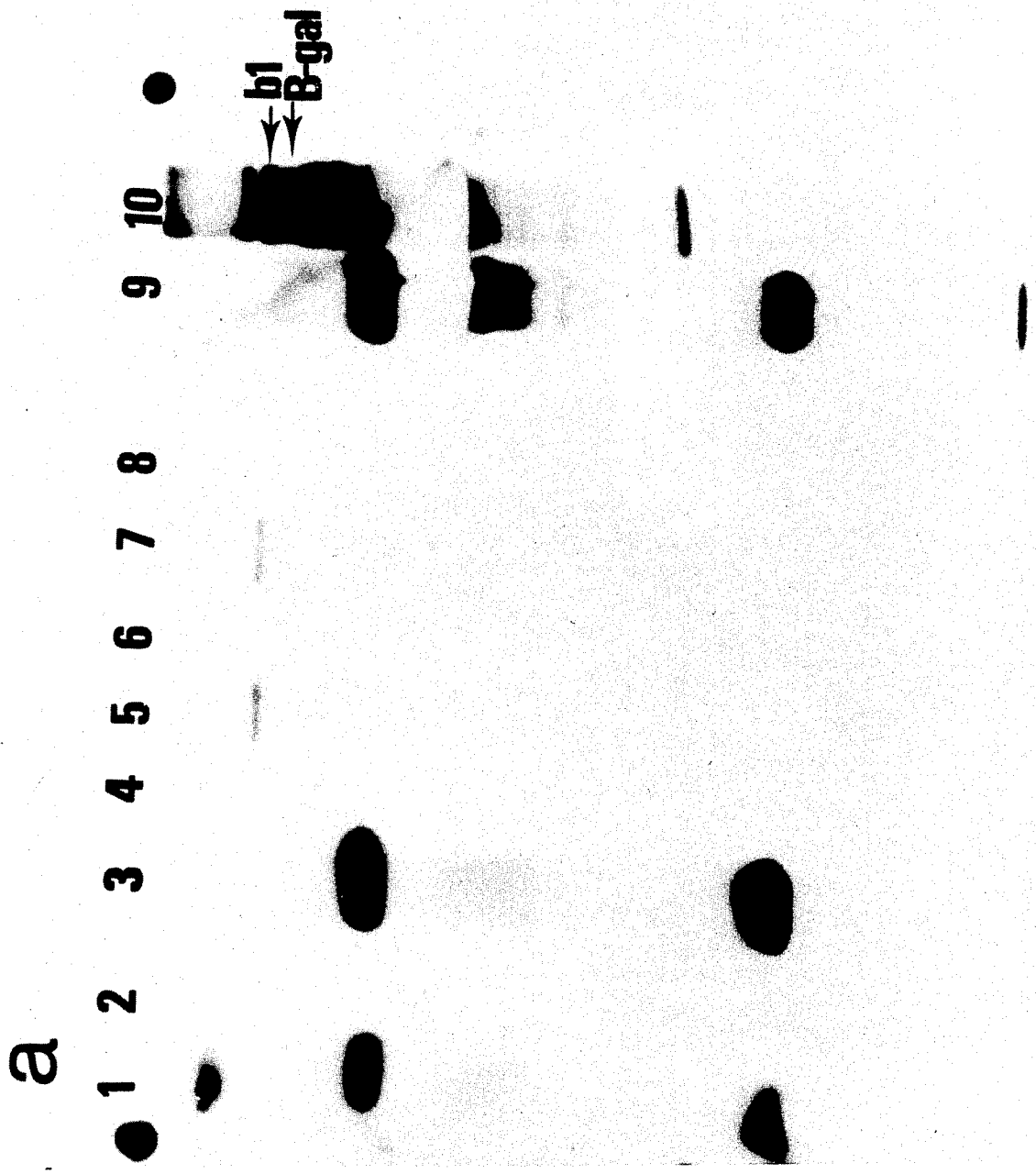
FIGS. 5a, b show autoradiograms of polyacrylamide gels depicting fusion proteins, (b1, and C21) specifically immunoprecipitated by antibodies directed against influenza hemagglutinin protein.
Figure 5B:
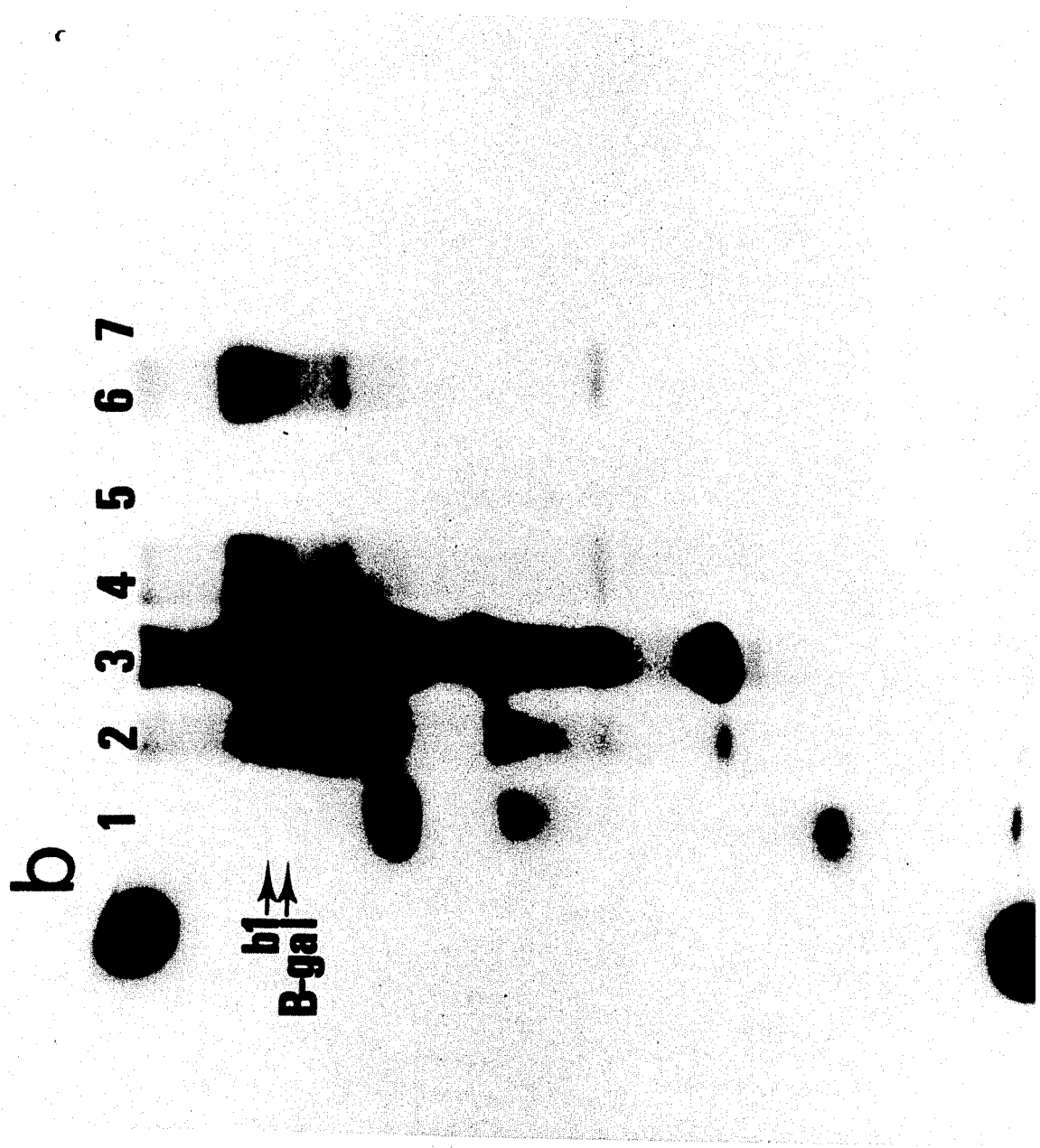

Iodinated fractions enriched in fusion proteins were incubated with anti-WSN IgG and immune complexes precipitated with protein A-Sepharose, eluted, and fractionated on SDS-polyacrylamide gels. FIG. 5a shows that viral HA (uncleaved) and M proteins were specifically precipitated by anti-WSN IgG (lanes 1 and 3) and were not precipitated in the absence of antiserum or in the presence of normal rabbit IgG (lanes 2 and 4, respectively). In addition, fusion protein b1 (calc. MW 131,639) was specifically precipitated by anti-WSN IgG (lanes 5 and 7) but not in the absence of antiserum or in the presence of normal rabbit IgG (lanes 6 and 8, respectively). When the enriched fraction of E. coli K-12 strain 294/pHBFc21 was precipitated, at least three proteins ranging in MW from 130,000-160,000 were precipitated in the presence of anti-WSN IgG (FIG. 5b, lanes 4 and 6), whereas no proteins were precipated in the absence of antiserum or in the presence of normal rabbit IgG (FIG. 5b, lanes 5 and 7, respectively).

Figure 6A:
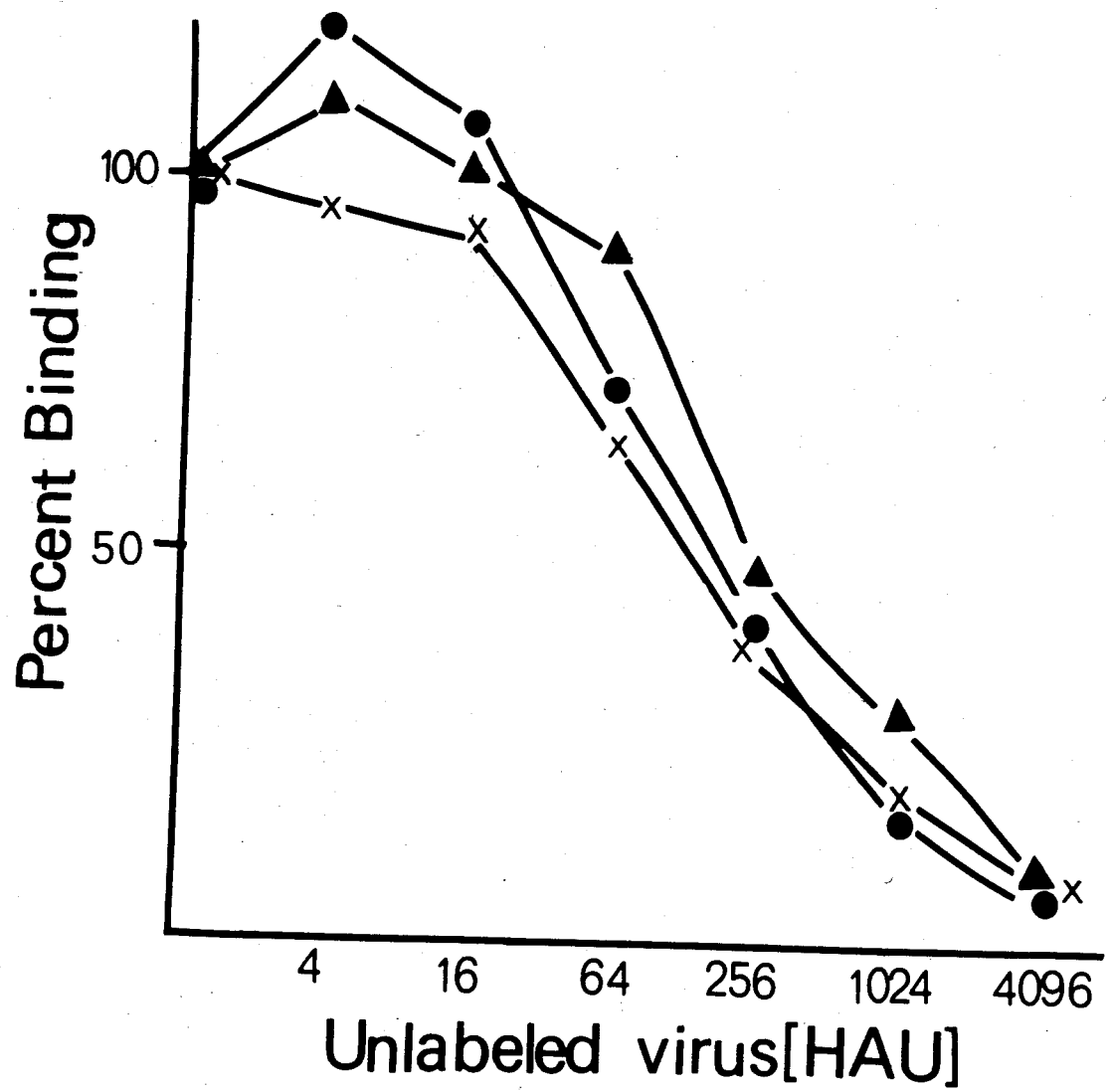
FIGS. 6a, b, c, and d show a graphical analysis and autoradiographs of polyacrylamide gels demonstrating that natural influenza hemagglutinin competes with the fusion proteins (b1 and c21) for antibodies directed against the viral proteins.
Figure 6B:
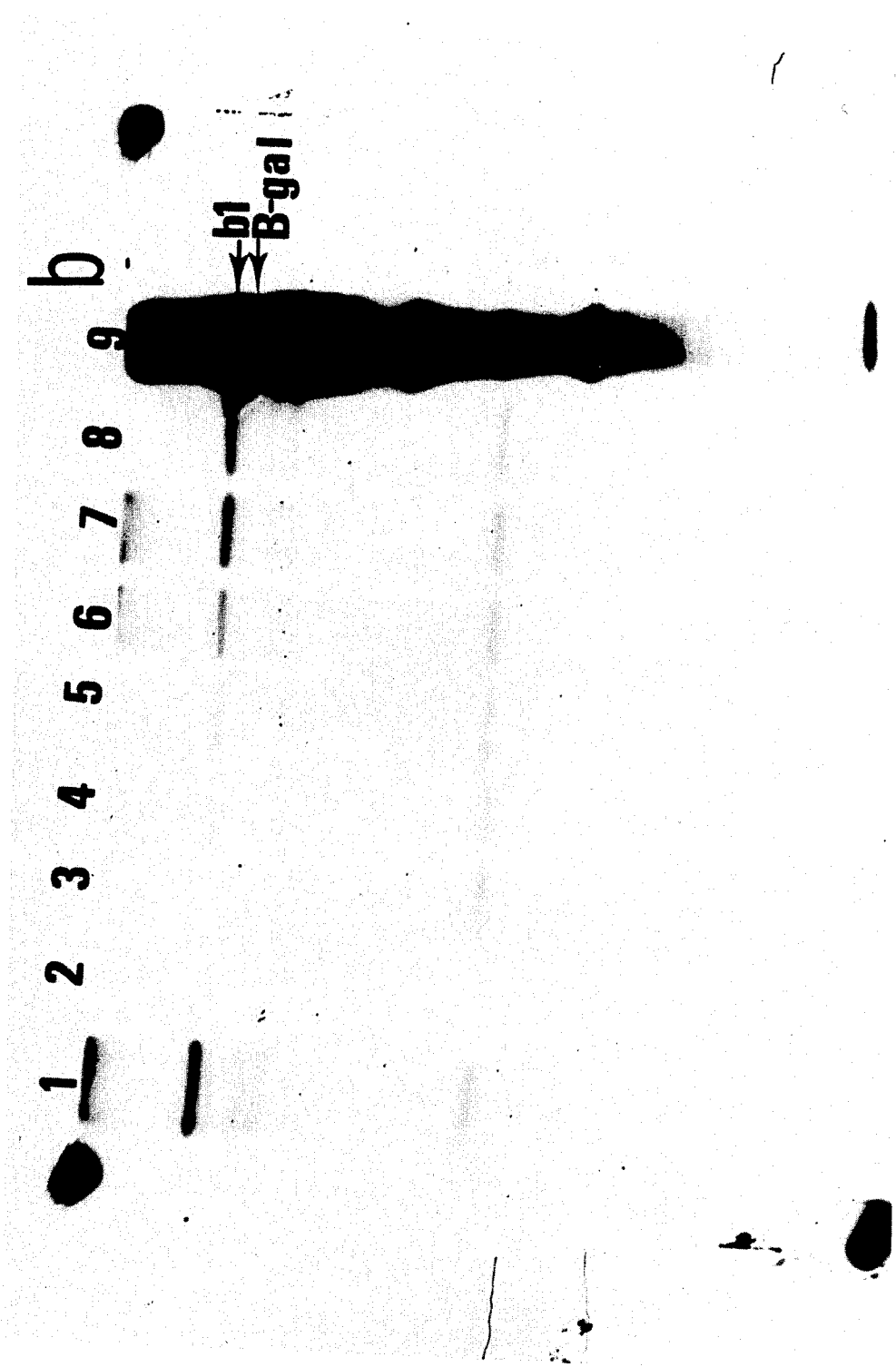
Figure 6C:
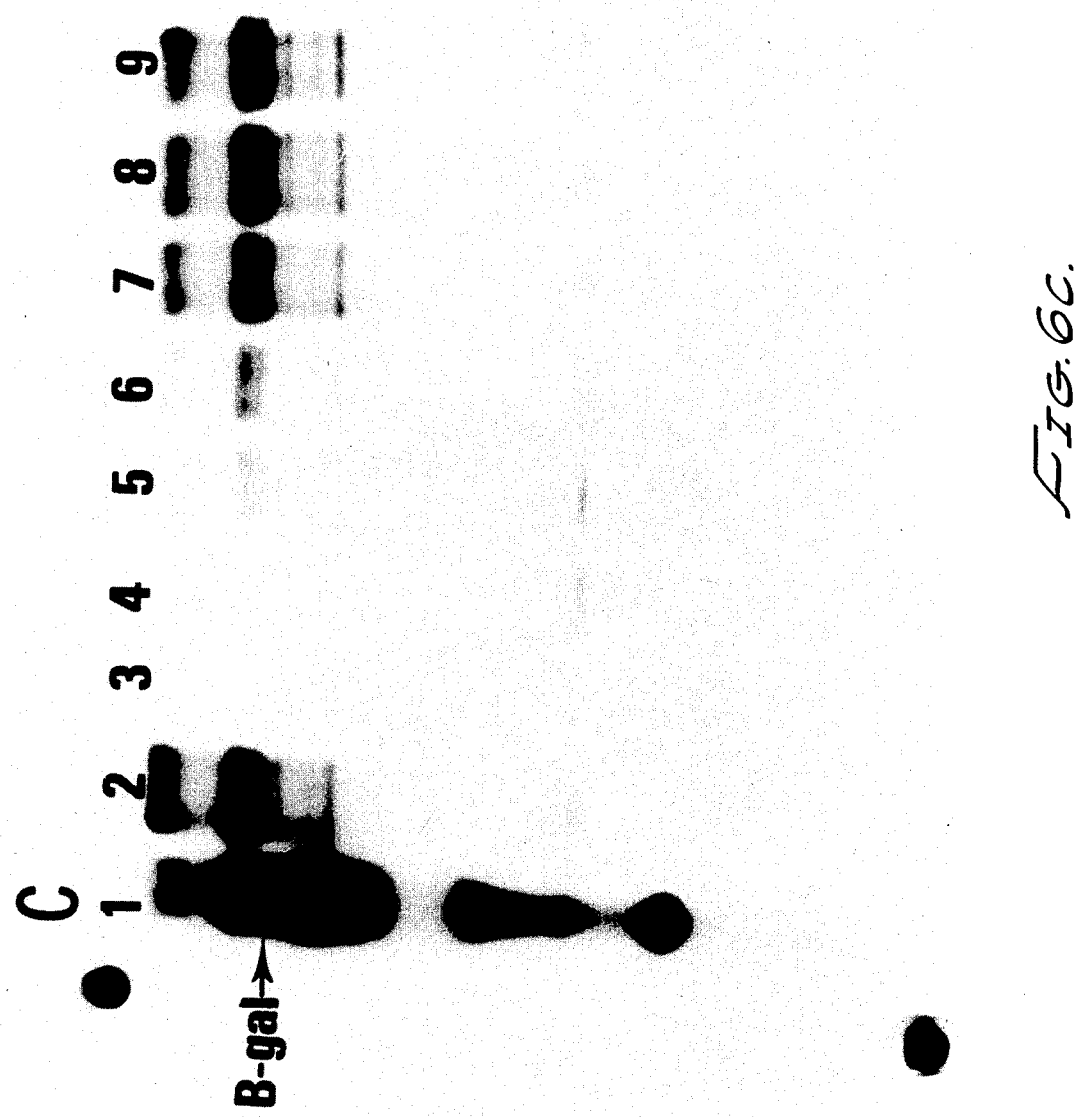
Figure 6D:
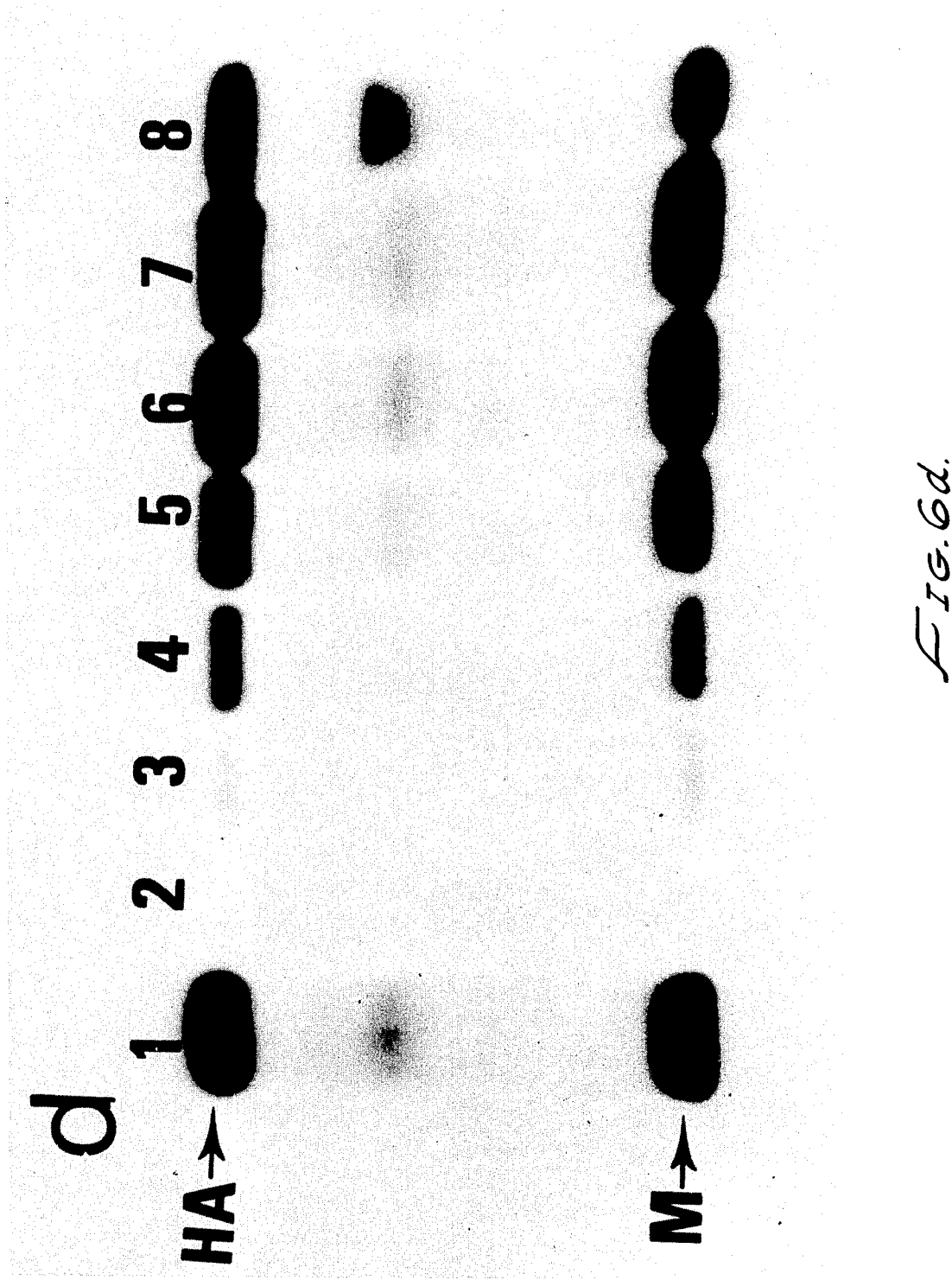
Figure 7A:
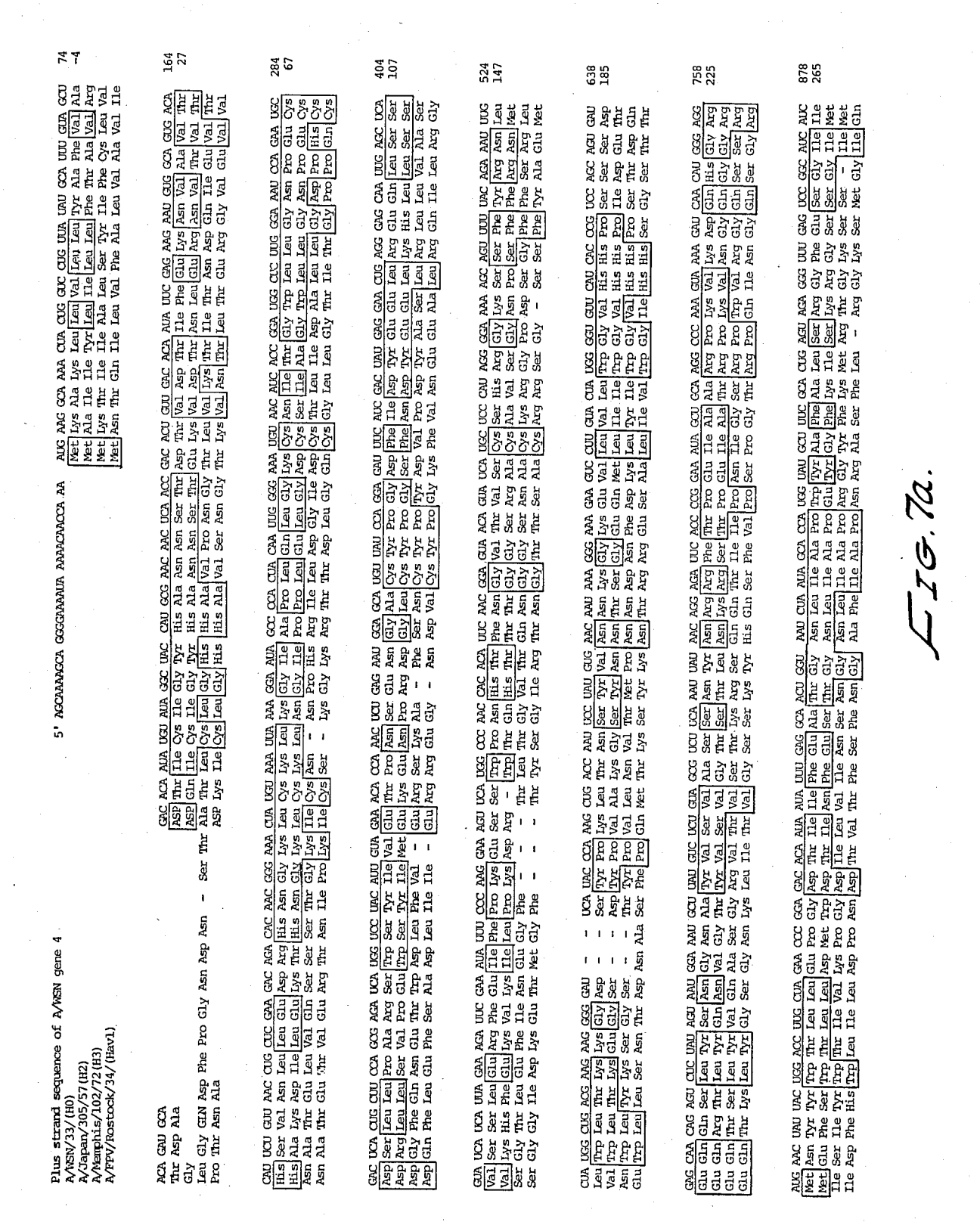
Figure 7B:
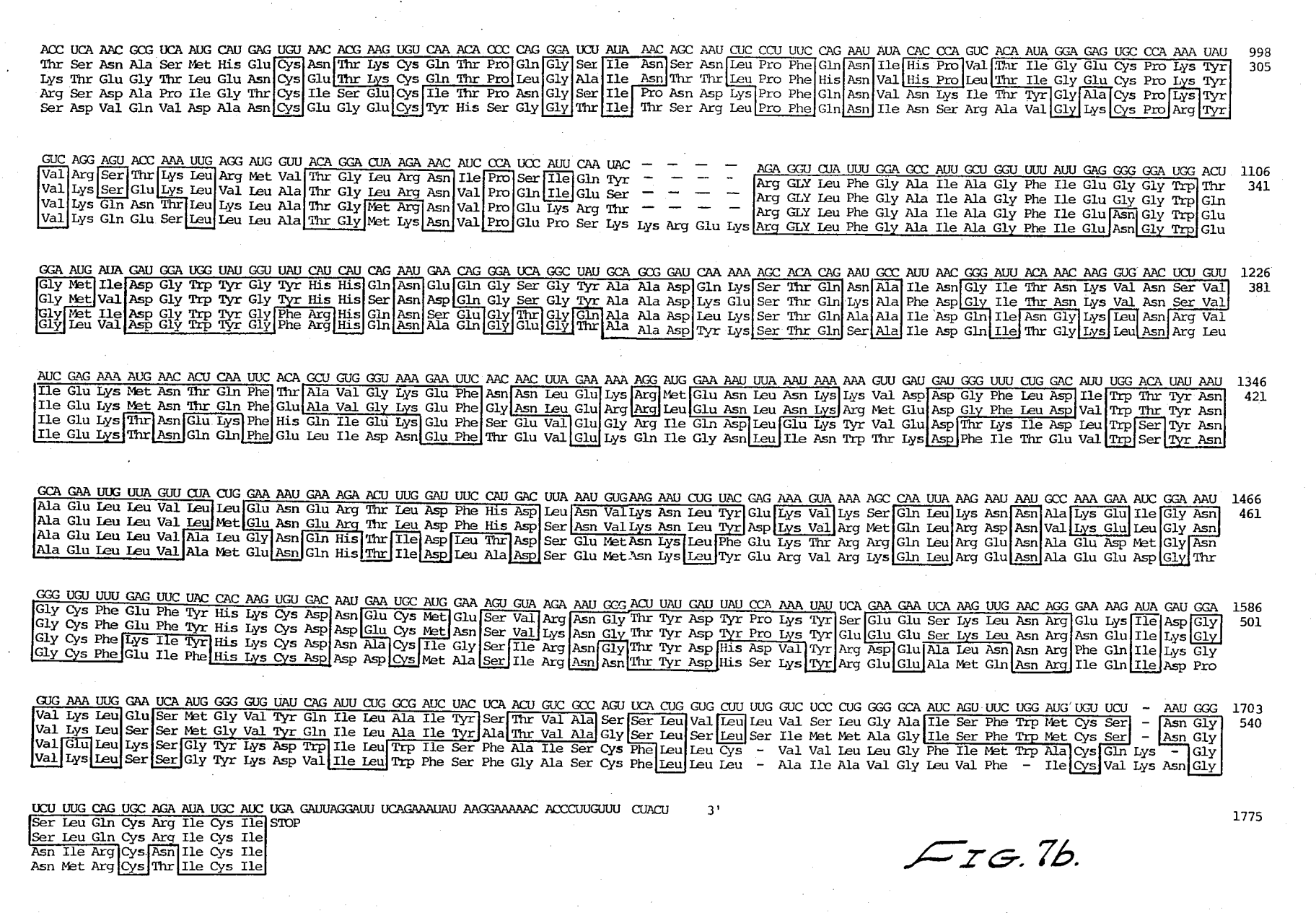

To further confirm that the fusion proteins are antigenically related to viral HA, anti-WSN IgG first incubated with varying amounts of unlabelled virus (4 to 4096 HAU) was used for determining the amount of binding to protein A-Sepharose of $^{125}I$ WSN virus, $^{125}I$ b1 protein, and $^{125}I$ c21 protein. FIG. 6a shows that unlabelled WSN virus can block 90-95 percent of formation of immune complexes in all three cases. Using the value at 50 percent competition we calculated that both E. coli K-12 strain 294/pHBFc21 and b1 produce approximately 8-10 μg fusion protein/ml in uninduced culture and two to three-fold more in cultures induced with IPTG. Immune complexes formed at each concentration of unlabelled virus were eluted from the protein A-Sepharose and analyzed on SDS-polyacrylamide gels. FIG. 7b shows that the unlabelled virus specifically competes with the formation of immune complexes of the b1 fusion protein, while FIG. 7c shows that unlabeled virus specifically competes with the formation of immune complexes of at least three c21 fusion proteins in the MW range 130,000-160,000. However, the binding of the small protein (MW 43,000) present in the $^{125}I$ c21 immune complex is not competed by unlabeled WSN virion, suggesting that this small protein may not be HA-specific. This protein represents less than 5 percent of the total protein immunoprecipitated.

Finally, the ability of fusion proteins to remove antihemagglutinin antibodies was tested. Accordingly anti-WSN IgG prepared in rabbits was adsorbed with the cell pellet fraction of E. coli K-12 strain 294/pHBFc20, c21, and b1 and the remaining antibodies titrated by hemagglutination inhibition assay (HI). Results (Table 1) show that the c21 protein removed at least 90 percent of the antibody while b1 protein removed less than 50 percent of the HI antibodies. Moreover, pellet fractions obtained from E. coli K-12 strain 294/pHBFc20 (reverse orientation) did not adsorb antibody. These results suggest that the c21 fusion protein contains more antigenic determinants than the b1 fusion protein, as expected.

TABLE 1

Adsorption of Anti-WSN Virus IgG with c21 and b1 Fusion Proteins

| Treatment | HI Titer[1] Exp. I | Exp. II |
|---|---|---|
| No adsorption | 512 | 128 |
| Adsorbed with E. coli 294/pHBFc20 cell pellet | | |
| 10 μl | 512 | — |
| 100 μl | 256 | — |
| 1000 μl | 512 | 128 |
| Adsorbed with E. coli 294/pHBFb1 cell pellet | | |
| 10 μl | 512 | — |
| 100 μl | 512 | — |
| 1000 μl | 256 | 64 |
| Adsorbed with E. coli 294/pHBFc21 cell pellet | | |
| 10 μl | 512 | — |
| 100 μl | 128 | — |
| 1000 μl | 8 | 8 |

Figure 4:
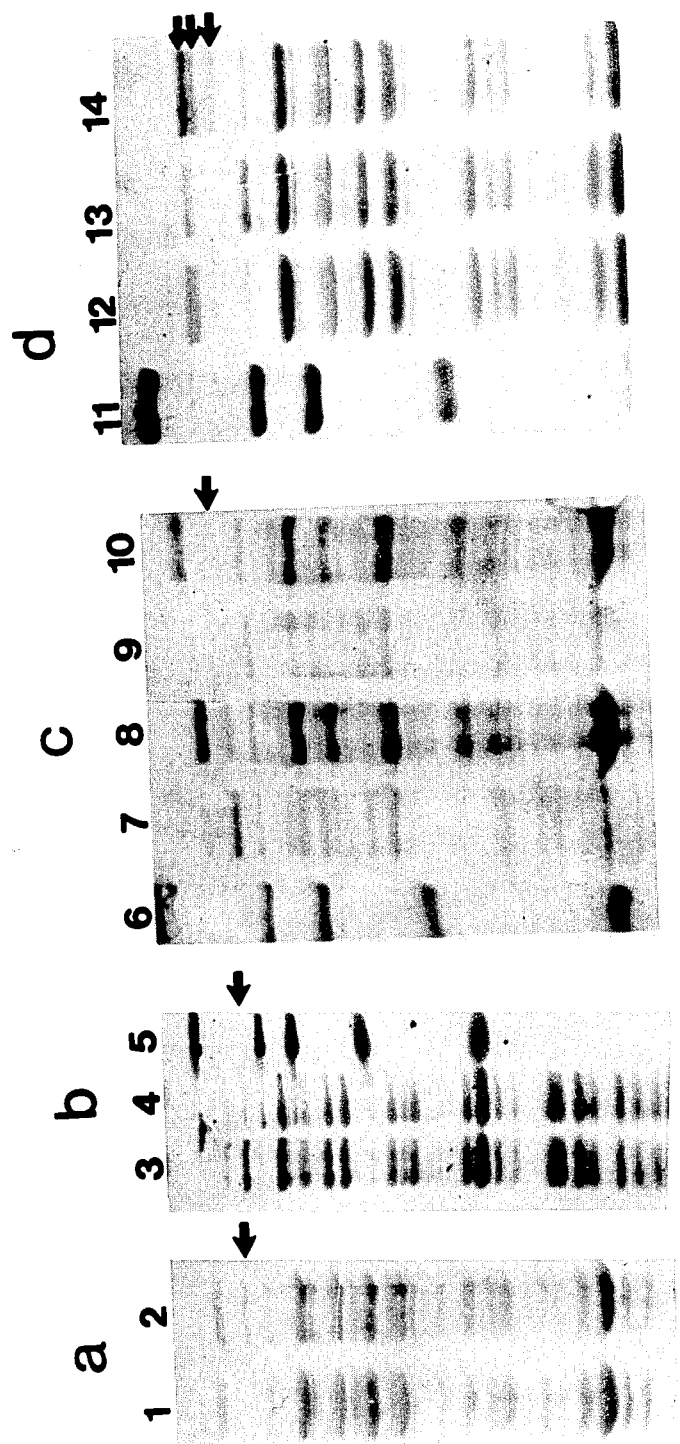
FIG. 4 depicts photographs of polyacrylamide gels depicting the proteins synthesized from E. coli 294/pHBFb1 and E. coli 294/pHBFc21 under various growth conditions.

[1]HI titer was measured in duplicate by the microtest system.
[2]Cell pellets were prepared from 1 liter culture as described in the legend to Fig. 4 and resuspended in 6 ml PBS. The volume of cell pellet shown was incubated with either 512 (Exp. 1) or 128 (Exp. 2) HI units anti-WSN virus IgG and cell pellet centrifuged, and the HI activity remaining in the supernatant measured.

In summary, these expression plasmids were shown to have the following properties. They directed the synthesis of fusion proteins of the correct size only when HA genes of proven sequence were in the correct orientation. The amount of each of these proteins is enchanced by IPTG, thus demonstrating their control by the lac operon. Each of the fusion proteins is specifically precipitated by antibody to WSN virus, indicating the presence of antigenic determinants and the immunoprecipitation of each of these proteins can be competed completely by excess virus. Finally, the largest fusion protein (c21) can remove a significant portion of the HI antibodies from rabbit antisera.

To express HA antigenic determinants in E. coli, the nucleotide sequences coding for the 5' untranslated region of cRNA and the 17 amino acid prepeptide were removed. This construction was accomplished by utilizing a synthetic deoxyoligonucleotide which primed the synthesis of the double-stranded HA DNA beginning precisely with the coding sequence of mature HA. The primer used for synthesis also carried on it the ATG initiation codon.

Two plasmids in which HA was fused in the correct amino acid reading frame to β-galactosidase were constructed. In one, the HA with a Met placed before it (pHBFc21) would yield a 226 amino acid CNBr peptide containing only HA sequences. The codons, 1-396, fused to the β-galactosidase gene contains AUG (met) at codon 226. In other studies, the large CNBr peptide of HA1 (amino acids 1-170) in H3N2 virus has been shown to be immunogenic. In the second construction (pHBFb1), fusion protein was constructed containing a smaller portion of HA1 (codons 59-211). This fusion yielded a polypeptide containing 152 amino acids of the HAI sequence, the region of the HA1 sequence that appears to contain most of the influenza antigenic sites in H3 and in HO.

A Vaccine for Influenza

This invention relates to a method whereby antigenic proteins, specifically the influenza hemagglutinin proteins or portions thereof, can be produced in useful quantities from microorganisms containing specific plasmid vehicles. The utility of this invention relates to the ability to convert these antigenic proteins to vaccine products, and the subsequent applications of these products for the prevention and/or treatment of the disease influenza in the human. The embodiments of this invention demonstrate that the produced material possesses the desired antigenic properties. The fusion proteins produced by the microorganism can be isolated and purified, alternatively, isolated, treated with cyanogen bromide (a reagent that cleaves proteinaceous material at methionine residues) and the released antigenic peptides purified (Wetzel et al. Supra). The lack of methionine residue within the antigenic regions of all of the various human influenza hemagglutinins makes this method particularly attractive. In the H3 virus, the hemagglutinin thus treated with cyanogen bromide releases a large peptide fragment from the antigenic region. This peptide elicits neutralizing antibodies (Jackson et al. *Virology* 93, 458 (1979) and contains the majority of the important antigenic determinants (Wiley et al. Supra). Isolation of such a peptide from a microorganism utilizes technology previously reported (Goeddel et al. Supra). Antigenic peptides have been shown to be useful in vaccine preparations (Mozes et al., *Proc. Natl. Acad. Sci.* (USA) 77, 4933 (1980).

The vaccines of the present invention, incorporating a polypeptide of HA protein, expressed as herein described, can be prepared according to known methods, where the polypeptide hereof is combined in admixture with a pharmaceutically acceptable vehicle. Suitable vehicles and their formulation are described in Remington's *Pharmaceutical Sciences* by E. W. Martin, which is hereby incorporated by reference. Such vaccines will contain an effective amount of the polypeptide hereof together with a suitable amount of vehicle in order to prepare an effective vaccine for effective administration to the host. Attention is also directed to *New Trends and Developments in Vaccines*, Editors: A. Voller and H. Friedman, University Park Press, Baltimore, 1978, which is hereby incorporated by reference, for further background details on the preparation of vaccines.

Such a vaccine is likely to be free of other viral and cellular components and is therefore less likely to produce pyrogenic reaction, Guilliam Barne syndrome, and other complications of whole killed or attenuated virus vaccine preparations.

While the invention in its most preferred embodiment is described with reference to *E. coli*, other microorganisms could likewise serve as host cells, for example, Bacilli such as *Bacillus subtilis* and preferably other enterobacteriaceae among which may be mentioned as examples *Salmonella typhimurium* and Serratia marcesans, utilizing plasmids that can replicate and express heterologous gene sequences in these organisms. Again, yeast may be employed as host organism in expressing the hemagglutinin proteins under the control of a yeast promoter. See the copending U.S. patent application of Ronald Hitzeman et al. filed Feb. 25, 1981, assignee Genentech, Inc. et al. Ser. No. 237,913, which is incorporated herein by reference. Thus, the invention is not to be limited to the preferred embodiments described, but only by the lawful scope of the appended claims.

EXAMPLES

Reagents

Restriction endonucleases were puchased from either New England Biolabs or Bethesda Research Labs and used as directed. *Escherichia coli* K12 strain 294 (endA thi−, hsr−, hsm$_k$−) was used for transformation herein (Backman, et al. Supra); ATCC No. 31446. Cells were transformed by the method of Seeburg, et al. Supra. Plasmid DNA was prepared from the lysate as described by Clewell, et al., Supra, followed by purification on a Biogel A50m column (Biorad). For small scale purification of plasmid DNA (miniscreen) the procedure of Birnborn and Daly, Supra was used. Restriction fragments were fractionated on either 1.4 percent agarose gels, prepared using low gelling temperature agarose or 5 percent acrylamide, 0.16 percent bisacrylamide gels in 90 mM tris-borate buffer (pH 8.3), 2.5 mM EDTA. DNA was eluted from agarose gels by melting the agarose as previously described (Davis, et al., Supra; Hiti, et al., Supra) and from polyacrylamide gels by electroelution. DNA was sequenced by the method of Maxam and Gilbert, Supra. Proteins were fractionated on 8 percent polyacrylamide gels using tris-glycine buffer and sodium dodecyl (SDS) (Laemmli, *Nature* (London) 227, 680). Samples were heated 2 min at 90° C. in 0.0625 M tris-HCl (pH 6.8), 2 percent SDS, and 5 percent 2-mercaptoethanol (sample buffer) before application.

Experimental Details of the Construction of a DNA Molecule Coding for Mature HA Construction of an HA DNA fragment starting with the codon for methionine followed by the coding sequence of mature HA, is depicted in FIG. 1.

The primer dAATGGACACAATATGT was synthesized by the improved phosphotriester method (Crea, et al., *Proc. Natl. Acad. Sci* (USA) 75, 5765 (1978)) using trideoxynucleotides as building blocks. It was then phosphosylated using ($\gamma$-$^{32}$P) ATP and polynucleotide kinase as previously described (Goeddel, et al., Supra. 1979). However, after 20 min, at 37° C. 16 nmole ATP was added and the reaction allowed to proceed an additional 10 min at 37° C. The plasmid pHA2-29 (50 μg) was treated with Pst 1, extracted with an equal volume of phenol and chloroform, and precipitated with ethanol. DNA was then treated with 2.0 units of λ exonuclease (New England Biolabs) in a reaction containing sodium glycine buffer, pH 9.6, 67 mM; MgCl$_2$, 3 mM; 2-mercaptoethanol, 3 mM for 30 min 37° C. $^{32}$P- primer (0.6 μg) was then added and the mixture extracted with phenol and chloroform and precipitated with ethanol. DNA and $^{32}$P-primer were resuspended in a buffer containing potassium phosphate, pH 7.4, 50 mM; 2-mercaptoethanol, 1 mM; and MgCl$_2$, 7 mM; and heated 4 min at 95° C. The reaction mixture was then adjusted to 0.5 mM in dATP, dGTP, dCTP, and dTTP and 3 units of DNA polymerase 1, Klenow fragment (New England Biolabs) added. After 30 min at 0° C., the reaction was allowed to proceed 16 h at room temperature. Finally, the DNA was isolated with phenol and chloroform, precipitated with ethanol, cleaved with Sst 1 and fractionated on a 5 percent poly acrylamide gel. The labeled 318 bp fragment was electroeluted.

The inset in FIG. 1 shows an autoradiogram of a polyacrylamide gel eletrophoresis of an Sst 1 digest of the primer-repair reaction product. The arrow marks the position of the 318 bp fragment.

Partial Purification of Fusion Proteins

Proteins systhesized from plasmids pHBFb1 and pHBFc21. Bacteria harbouring plasmids (1 ml) were grown to late log (A$_{550}$ if 1.0) in L-broth with ampicillin and collected by centrifugation. Cell pellets were resuspended in SDS sample buffer (Laemmli, Supra) and proteins visualized by staining with Comassie blue. The position of hybrid proteins b1 and c21 are indicated by arrows in FIG. 4. (a) Lane 1, pHBFb9; lane 2 pHBFb1. (b) Lane 3, cells harbouring pHBFb1 were grown in the presence of 2 mM IPTG; lane 4, pHBFb1 without IPTG; lane 5, marker proteins, top to bottom myosin, 200,000; β-galactosidase, 116,350; phosphorylase B, 94,000; bovine serum albumin, 68,000; and ovalbumin, 43,000. (c) Bacteria harbouring plasmids were grown as above, resuspended in 1 ml lysis buffer (Wetzel, et al., Supra), and disrupted by sonication. Cell debris and insoluble protein were pelleted by centrifugation at 27,000×g for 30 min. Lane 6, marker proteins; lane 7 pHBFb1 pellet; lane 8, pHBFb1 supernatant; lane 9, pHBFb9 pellet; lane 10, pHBFb9 supernantant. (d) Cells harbouring plasmid pHBFc20 or 21 were grown as described above and the total proteins fractionated. Lane 11, marker proteins; lane 12, pHBFc21; lane 13, pHBFc20, 2 mM IPTG; lane 14, pHBFc21, 2 mM IPTG.

Immunoprecipitation of Hemagglutinin Fusion Proteins

Fusion proteins were partially purified by a modification of the procedure of Wetzel, et al., Supra. Thirty grams wet cell paste was suspended in 135 ml lysis buffer (10 percent sucrose, 0.2 M NaCl, 50 mM EDTA, 100 mM tris-HCl (pH 7.9), and 740 units/ml Traysylol (Calbiochem). Cells were lysed by one passage through a French press at 8000 bl/in$^2$. The lysate was centrifuged 30 min at 24,000×g and the pellet resuspended in 100 ml 7M guanidine hydrochloride by stirring 16 h at 4° C. After centrifugation for 30 min at 24,000×g, proteins in the supernatant were precipitated by the addition of 10 volumes of cold water. Proteins were collected by centrifugation for 30 min at 2600×g. The pellet was dissolved by heating 2 min at 90° C. in 2 percent SDS, 5 percent 2-mercaptoethanol. A portion of the dissolved protein was fractionated on a column of Sephacryl S-200 equilibrated with 0.25 M tris-borate buffer (pH 8.9), 0.016 M EDTA, 0.4 percent SDS. Protein that eluted in the void volume was enriched in fusion protein as determined by electrophoresis on polyacrylamide—SDS gels. These gels are depicted in FIGS. 5a, b.

WSN virus was disrupted with 2 percent SDS and iodinated using chloroglycoluril (Markwell and Fox, Biochemistry 17, 4807 (1978). Additionally a protein fraction enriched in fusion protein b1 was iodinated. Antiserum against WSN virus was prepared in rabbits and IgG was prepared by precipitation with 50 percent and 33 percent saturated amonium sulfate followed by purification on a DEAE cellulose column. Anti-WSN IgG and $^{125}$I b1 fraction were then incubated overnight at 4° C. in a 400 ml immunoprecipitation buffer (0.15 M NaCl, 1 percent sodium deoxycholate, 1 percent triton-X-100, 0.1 percent SDS, 10 mM tris-HCl (pH 7.4), 1 mM phenylmethylsulfonylfluoride) as described (Lamb, et al., Virology 91, 60 (1978)). Immune complexes were precipitated by addition of 4 mg protein A-Sepharose (Pharmacia) and incubation for 1 h at 0° C. Unbound proteins were removed by four washes in microcentrifuge 2 min each with 1 ml immunoprecipitation buffer. Bound immune complexes were disrupted by heating 2 min at 90° C. in SDS sample buffer and analyzed on an 8 percent SDS polyacrylamide gel. (See FIG. 5a.) Lane 1, $^{125}$I WSN virus with 10 μl anti-WSN virus IgG; lane 2, $^{125}$I WSN virus without IgG; lane 3, $^{125}$WSN virus with 20 μl anti-WSN virus IgG; lane 4, $^{125}$+WSN virus with 20 μl normal rabbit IgG; lane 5, $^{125}$I fraction enriched in b1 protein and 10 μl anti-WSN virus IgG; lane 6, $^{125}$I fraction enriched in b1 protein without IgG; lane 7, $^{125}$I fraction enriched in b1 protein with 20 μl anti-WSN virus IgG; lane 8, $^{125}$I fraction enriched in b1 protein with 20 μl normal rabbit IgG. Lanes 9 and 10 show total $^{125}$I WSN virus and the $^{125}$I fraction enriched b1 fusion protein, respectively.

A protein fraction enriched in fusion protein c21 was iodinated and is analyzed in FIG. 5b. Lanes 1, 2 and 3 show the fractionation of $^{125}$I WSN virus, $^{125}$I fraction enriched in fusion protein b1, and $^{125}$I fraction enriched in fusion protein c21, respectively. $^{125}$I c21 fraction was incubated overnight in immunoprecipitation buffer as follows: Lane 4, 10, μl anti-WSN virus IgG; lane 5, no IgG; lane 6, 20 μl anti-WSN virus IgG; lane 7, normal rabbit IgG.

Competition of Immunoprecipitation of β-Galactosidase-HA Fusion Protein with WSN Virus FIG. 6a depicts an experiment where anti-WSN virus IgG (10 μl pf a 1:2 dilution for virus-virus competition and 10 μl of a 1:4 dilution for virus-fusion protein competition) was incubated with 4 to 4096 HA units of virus for 5 h at 4° C. in immunoprecipitation buffer. Then either $^{125}$I WSN virus (0), an $^{125}$I fraction enriched in b1 fusion protein (X), or an $^{125}$I fraction enriched in c21 fusion protein (Δ) was added and incubation was continued for 16 h at 4° C. Protein A Sepharose was added and samples immunoprecipitated as described above. Percentage binding was calculated from cpm bound to protein A Sepharose. CPM for 100 percent binding WSN virus, 143,692; b1, 25,343 cpm; and c21, 137,165 cpm. After proteins were eluted from protein A-Sepharose they were analyzed in polyacrylamide-SDS gels. These gels are shown in FIGS. 6, b, c, and d.

(6b) Polyacrylamide-SDS gel analysis of the competition of b1. Lane 1, no competing virus; lane 2, normal IgG; lane 3 through 8, 4096, 1024, 256, 64, 16 and 4 HA units virus, respectively; lane 9, $^{125}$I b1 fraction.

(6c) Polyacrylamide-SDS gel analysis of the competition of c21. Lane 1, $^{125}$I c21 fraction; lane 2, no competing virus; lane 3, normal IgG; lanes 4 through 9, 4096 1024, 256, 64, 16, and 4 HA units virus, respectively.

(6d) Polyacrylamide-SDS gel analysis of the competition of WSN virus. Lane 1, no competing virus; lane 2, normal IgG; lanes 3 through 7, 4096, 1024, 256, 64 land 16 HA units virus, respectively; lane 8, $^{125}$I WSN virus.

We claim:

1. A replicable microbial expression vehicle containing a promoter-operator sequence capable of expressing heterologous proteins in a microorganism, and a methionine codon followed by DNA encoding at least one antigenic determinant of human influenza hemagglutinin, wherein transcription of said DNA in a transformant microorganism is under control of said promoter-operator sequence, and wherein said DNA lacks the sequence of the prepeptide of the human influenza hemagglutinin.

2. A transformant microorganism comprising the expression vehicle according to claim 1.

3. The expression vehicle according to claim 1, wherein said promoter-operator sequence comprises a lac operon.

4. An expression vehicle according to claim 1 wherein said promoter-operator sequence comprises a tryptophan operon.

5. The expression vehicle according to claim 3 wherein said determinant comprises amino acids 1 to 396 of human influenza hemagglutinin protein fused via a methionine to the first 1,005 amino acids of the beta-galactosidase of the lac operon.

6. The expression vehicle acccording to claim 3 wherein said determinant comprises amino acids 59 to 211 of human influenza hemagglutinin protein fused to the first 1,005 amino acids of the beta-galactosidase of the lac operon.

7. The expression vehicle according to claim 4 wherein said determinant comprises amino acids 1 to 396 of human influenza hemagglutinin proteins fused via a methionine to amino acids 1 to 190 of said tryptophan operon.

8. The expression vehicle according to claim 4 wherein said determinant comprises amino acids 1 to 211 of human influenza hemagglutinin protein fused via a methionine to the first 190 amino acids of the polypeptide of said tryptophan operon.

9. The expression vehicle according to claim 3 wherein said determinant comprises amino acids 1 to 211 of human influenza hemagglutinin protein fused via a methionine to the first 1,005 amino acids of the beta-galactosidase of the lac operon.

10. The transformed microorganism *E. coli* comprising the expression vector of claim 1.

* * * * *